US010592820B2

(12) United States Patent
Cao et al.

(10) Patent No.: US 10,592,820 B2
(45) Date of Patent: Mar. 17, 2020

(54) SEQUENTIAL LEARNING TECHNIQUE FOR MEDICAL IMAGE SEGMENTATION

(71) Applicant: INTERNATIONAL BUSINESS MACHINES CORPORATION, Armonk, NY (US)

(72) Inventors: Yu Cao, San Jose, CA (US); Tanveer Syeda-Mahmood, Cupertino, CA (US); Hongzhi Wang, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 348 days.

(21) Appl. No.: 15/178,511

(22) Filed: Jun. 9, 2016

(65) Prior Publication Data

US 2017/0358075 A1 Dec. 14, 2017

(51) Int. Cl.
*G06K 9/00* (2006.01)
*G06N 20/00* (2019.01)
(Continued)

(52) U.S. Cl.
CPC ........... *G06N 20/00* (2019.01); *G06K 9/4642* (2013.01); *G06K 9/6278* (2013.01); *G06N 7/005* (2013.01);
(Continued)

(58) Field of Classification Search
CPC ......... G06T 2207/20081; G06T 7/0012; G06T 7/11; G06T 2207/20084; G06T 7/251;
(Continued)

(56) References Cited

U.S. PATENT DOCUMENTS 7,809,190 B2  10/2010 Rousson et al.
2006/0023927 A1*  2/2006 Zhang ...................... G06T 7/11
382/131
(Continued)

FOREIGN PATENT DOCUMENTS

CN  102436583  5/2012
CN  104036505  9/2014

OTHER PUBLICATIONS

Blei et al., Modeling Annotated Data, Jul. 28-Aug. 1, 2003, SIGIR'03, ACM , pp. 1-7.*
(Continued)

*Primary Examiner* — Vu Le
*Assistant Examiner* — Guillermo M Rivera-Martinez
(74) *Attorney, Agent, or Firm* — Schmeiser, Olsen & Watts, LLP

(57) ABSTRACT

Sequential learning techniques, such as auto-context, that apply the output of an intermediate classifier as contextual features for its subsequent classifier have shown impressive performance for semantic segmentation. It is shown that these methods can be interpreted as an approximation technique derived from a Bayesian formulation. To improve the effectiveness of applying this approximation technique, a new sequential learning approach is proposed for semantic segmentation that solves a segmentation problem by breaking it into a series of simplified segmentation problems. Sequentially solving each of the simplified problems along the path leads to a more effective way for solving the original segmentation problem. To achieve this goal, a learning-based method is proposed to generate simplified segmentation problems by explicitly controlling the complexities of the modeling classifiers. Promising results were reported on the 2013 SATA canine leg muscle segmentation dataset.

16 Claims, 18 Drawing Sheets

(51) Int. Cl.
*G06K 9/46* (2006.01)
*G06T 7/143* (2017.01)
*G06K 9/62* (2006.01)
*G06T 7/11* (2017.01)
*G06N 7/00* (2006.01)

(52) U.S. Cl.
CPC ............... *G06T 7/11* (2017.01); *G06T 7/143* (2017.01); *G06K 2209/051* (2013.01); *G06T 2207/20081* (2013.01); *G06T 2207/30004* (2013.01)

(58) Field of Classification Search
CPC ........... G06T 2207/30004; G06T 2207/30016; G06K 9/6256; G06K 2209/051; G06K 9/66; G06K 9/6267; G06K 9/6292; G06N 3/08; G06N 5/00
See application file for complete search history.

(56) References Cited

U.S. PATENT DOCUMENTS

| | | | | |
|---|---|---|---|---|
| 2006/0074834 A1* | 4/2006 | Dong | .................... | G06K 9/6256 706/45 |
| 2007/0253611 A1* | 11/2007 | Rousson | .................... | G06K 9/34 382/128 |
| 2010/0074499 A1* | 3/2010 | Wels | .................... | G06T 7/11 382/131 |
| 2010/0232686 A1* | 9/2010 | Dewan | ................ | G06K 9/6209 382/159 |
| 2010/0240996 A1* | 9/2010 | Ionasec | ................ | G06T 7/0016 600/443 |
| 2013/0223711 A1 | 8/2013 | Knapp et al. | | |
| 2013/0346346 A1 | 12/2013 | Criminisi et al. | | |
| 2014/0100485 A1* | 4/2014 | Linguraru | ............ | A61B 5/1075 600/587 |
| 2014/0148690 A1 | 5/2014 | Kim et al. | | |
| 2014/0233826 A1* | 8/2014 | Agaian | ................ | G16H 50/30 382/133 |
| 2014/0328527 A1* | 11/2014 | Zhou | .................... | G06K 9/66 382/131 |
| 2016/0148372 A1* | 5/2016 | Itu | .................... | G16H 50/50 382/128 |
| 2016/0174902 A1* | 6/2016 | Georgescu | ................ | G06T 7/73 600/408 |
| 2017/0357753 A1* | 12/2017 | Mori | .................... | G06T 7/0014 |

OTHER PUBLICATIONS

Anonymous, "Method for Atlas Reduction in Label Fusion-Based Segmentation," ip.com Prior Art Database Technical disclosure, Apr. 25, 2015, 7pgs.

Li et al., "Integrating Spatial Fuzzy Clustering With Level Set Methods for Automated Medical Image Segmentation," Computers in Biology and Medicine, 41(1), 2011, pp. 1-10.

Asman, et al., "MICCAI 2013 Segmentation Algorithms, Theory and Applications (SATA) Challenge Results Summary," MICCAI 2013 Challenge Workshop on Segmentation: Algorithms, Theory and Applications, Springer, 2013, 9pgs.

Avants et al., "Symmetric Diffeomorphic Image Neurodegenerative Brain," Medical Image Analysis, 12(1), 2008, pp. 26-41.

Cohen et al., "Stacked Sequential Learning," Proceedings of the IJCAI, Morgan Kaufmann Publishers Inc., 2005, pp. 671-676.

Freund et al., "A Decision-Theoretic Generalization of On-Line Learning and an Application to Boosting," Proceedings of the 2nd European Conference on Computational Learning Theory, Barcelona, Spain, Mar. 13-15, 1995, pp. 23-27.

Heckemann et al., "Automatic Anatomical Brain MRI Segmentation Combining Label Propagation and Decision Fusion," NeuroImage, v33, 2006, pp. 115-126.

Montillo et al., "Entangled Decision Forests and Their Application for Semantic Segmentation of CT Images," Information Processing in Medical Imaging, Springer, 2011, pp. 184-196.

Munoz et al., "Stacked Hierarchical Labeling," Computer Vision—ECCV 2010, Springer, 2010, pp. 57-70.

Rohlfing et al., "Quo Vadis, Atlas-Based Segmentation?" The Handbook of Medical Image Analysis: Segmentation and Registration Models, Kluwer, 2005, pp. 435-486.

Tu et al., "Auto-Context and Its Application to High-Level Vision Tasks and 3D Brain Image Segmentation," IEEE Trans. on PAMI, 32(10), Oct. 2010, pp. 1744-1757.

Tu et al., "Automated Extraction of the Cortical Sulci Based on a Supervised Learning Approach," IEEE TMI, 26(4), Apr. 2007, pp. 541-552.

Van Leemput et al., "Automated Segmentation of Hippocampal Subfields From Ultra-High Resolution in Vivo MRI," Hippocampus, v19, Apr. 29, 2009, pp. 549-557.

Wang et al., "Multi-Atlas Segmentation with Joint Lavel Fusion," IEEE Trans. on PAMI, 35(3), Mar. 2013, pp. 611-623.

Wang et al., "A Learning-Based Wrapper Method to Correct Systematic Errors in Automatic Image Segmentation: Consistently Improved Performance in Hippocampus, Coretx and Brain," Neuroimage, 55(3), Jan. 2011, pp. 968-985.

Wang et al., "Multi-Atlas Segmentation with Joint Label Fusion and Corrective Learning—an Open Source Implementation," Frontiers in Neuroinformatics, 7(27), Nov. 2013, 12pgs.

Wolpert, D., "Stacked Generalization," Neural Networks, 5(2), Jan. 1992, pp. 241-259.

* cited by examiner

Algorithm 1 Path sequential learning algorithm:

1: INPUT: A set of training images with segmentations $\{(I_i, L_i), i = 1, ..., m\}$.
2: for $t = 1$ to $T$ do
3:   Take the images and the segmentation results produced for each image in previous iterations, i.e. MAP segmentations $(S^1, ..., S^{t-1})$ + label posterior maps, as feature images, derive a simplified segmentation problem for the original segmentation problem, i.e. $\{(I_i, L_i^t), i = 1, ..., m\}$ (see details in section 2.6).
4:   Train classifier $C^t$ using all training images to solve the simplified problem.
5:   For the next iteration, produce MAP segmentation $S_i^t$ and label posterior maps for solving the simplified problem for each image using cross-validation.
6: end for
7: Train classifier $C^{T+1}$ using all training images to solve the original segmentation problem with images and the segmentation results produced above as features.
8: Returns the sequence of trained classifiers $(C^1, C^2, ..., C^T, C^{T+1})$.

FIG. 1A

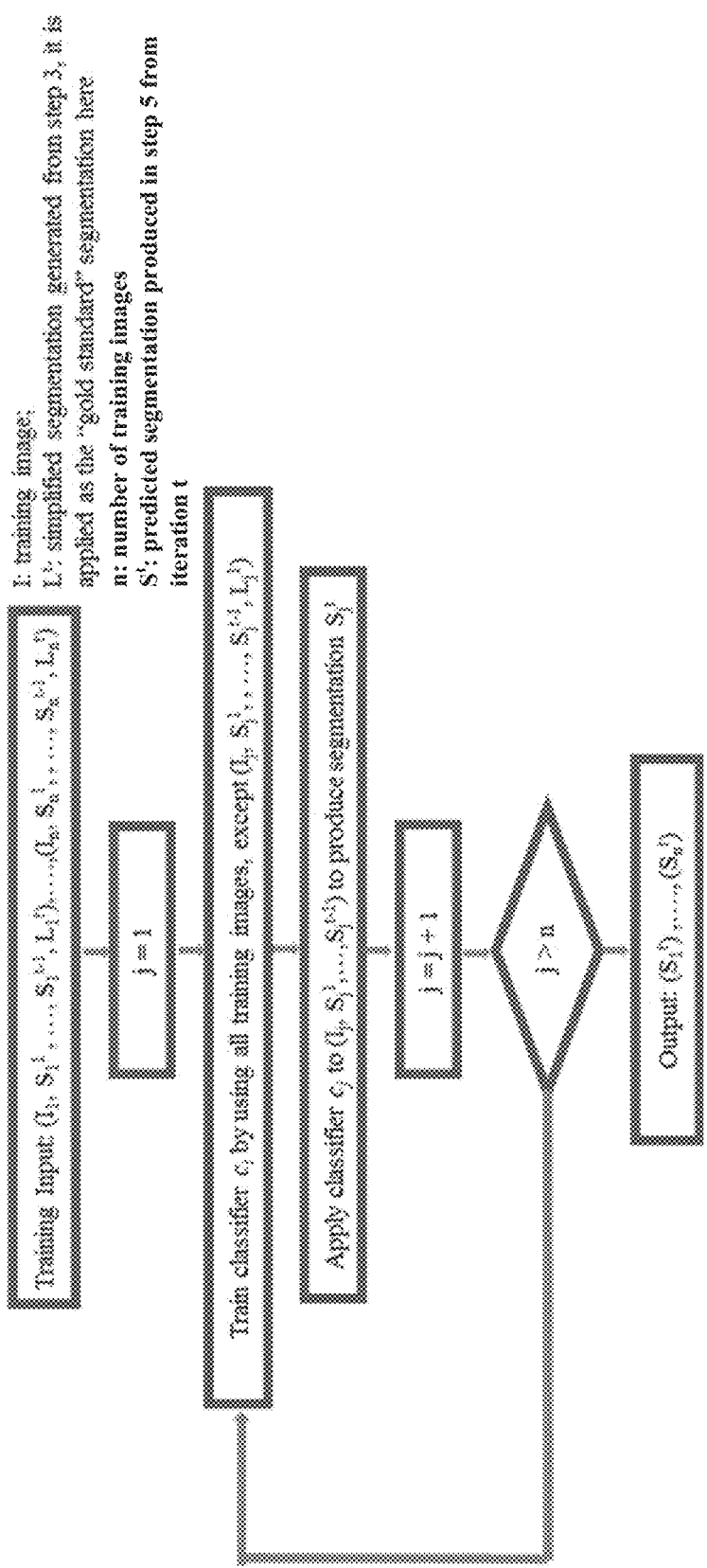

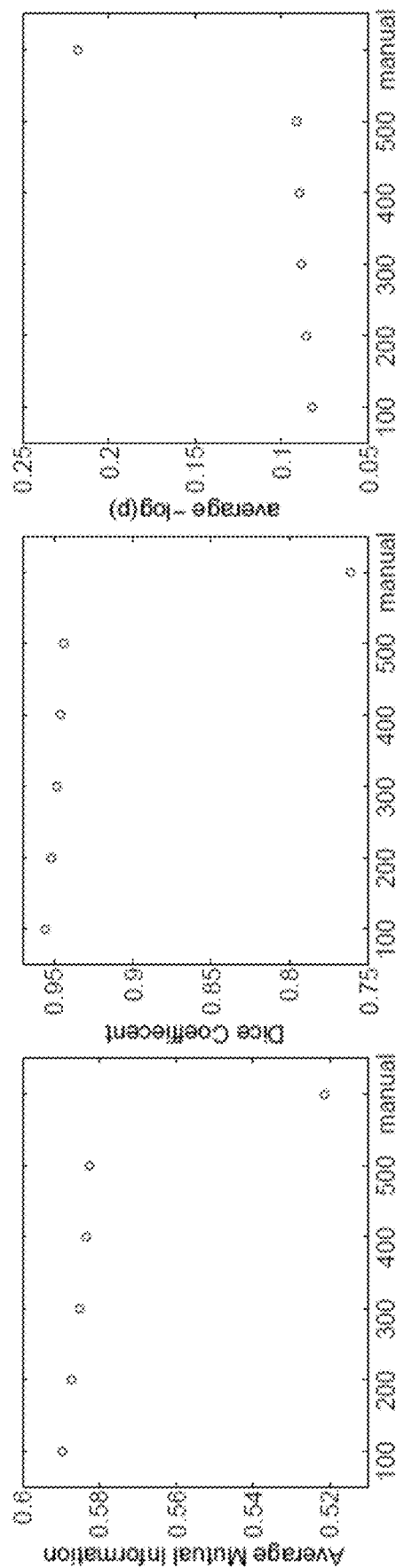

| anatomical region | JLF | Auto-context | Stacked | Path |
|---|---|---|---|---|
| CS | 0.564±0.168 | 0.580±0.208 | 0.606±0.198 | 0.595±0.208 |
| RF | 0.664±0.162 | 0.717±0.149 | 0.730±0.168 | 0.736±0.169 |
| SE | 0.855±0.062 | 0.870±0.074 | 0.871±0.065 | 0.875±0.068 |
| BF | 0.805±0.095 | 0.798±0.108 | 0.814±0.102 | 0.822±0.103 |
| GR | 0.832±0.052 | 0.803±0.036 | 0.865±0.034 | 0.870±0.035 |
| VL | 0.774±0.135 | 0.800±0.138 | 0.810±0.128 | 0.821±0.121 |
| AD | 0.646±0.142 | 0.654±0.158 | 0.667±0.149 | 0.675±0.153 |

FIG. 5

| Method | JLF | JLF+CL | Auto-context | Stacked | Path |
|---|---|---|---|---|---|
| Dice | 0.731(0.768) | 0.762(0.797) | 0.782(0.815) | 0.793(0.818) | 0.800(0.829) |

FIG. 7

SEQUENTIAL LEARNING TECHNIQUE FOR MEDICAL IMAGE SEGMENTATION

BACKGROUND OF THE INVENTION

Field of Invention

The present invention relates generally to the field of image segmentation. More specifically, the present invention is related to automatically producing anatomy segmentation for medical images through sequential learning.

Discussion of Related Art

Medical image segmentation is the problem of locating anatomical structures from medical images. While, in the prior art, simplified segmentation problems may be built through a coarse-to-fine hierarchical decomposition of regions for images using low level segmentation, such prior art methods do not address the complexities in learning models for solving these problems. Hence, there is no guarantee that the generated hierarchical segmentation problems can be more easily solved than the original problem.

Embodiments of the present invention are an improvement over prior art systems and methods.

SUMMARY OF THE INVENTION

One embodiment of the present invention discloses a medical image segmentation method for locating an anatomical structure in an image of interest to a user, using a training set of one or more annotated, anatomical images, the method comprising: (a) decomposing each annotated, anatomical image in the training set into a plurality of regions; (b) generating, for each annotated, anatomical image in the training set, a hierarchy that includes a plurality of levels, each level in the hierarchy corresponding to one of the plurality of regions; (c) obtaining, from storage, at least one previously derived annotation for each level in the hierarchy and training a plurality of first classifiers to approximate the previously derived annotations, wherein the first classifiers are trained in a particular sequence such that the output of one of the first classifiers becomes input to another one of the first classifiers; (d) storing the trained, first classifiers of (c); and (e) locating an anatomical structure in the image of interest to the user based on the stored trained, first classifiers.

In another embodiment, the present invention discloses a medical image segmentation method for locating an anatomical structure in an image of interest to a user, using a training set of one or more anatomical images, the method comprising: (a) decomposing each anatomical image in the training set into a plurality of regions; (b) generating, for each anatomical image in the training set, a hierarchy that includes a plurality of levels, each level in the hierarchy corresponding to one of the plurality of regions; (c) training, for each anatomical image in the training set, a plurality of first classifiers to approximate one or more annotations, and storing one or more such estimated annotations by the first classifiers as previously derived annotations; (d) training a plurality of second classifiers to approximate the previously derived annotations, where the second classifiers are trained in a particular sequence such that the output of one of the second classifiers becomes input to another one of the second classifiers; (e) storing the trained, second classifiers in (d); and (f) locating an anatomical structure in the image of interest to the user based on stored trained, second classifiers.

In yet another embodiment, the present invention provides an article of manufacture comprising non-transitory computer storage medium storing computer readable program code which, when executed by a computer, implements a computer-based medical image segmentation method for locating an anatomical structure in an image of interest to a user, using a training set of one or more annotated, anatomical images, the method comprising: (a) computer readable program code decomposing each annotated, anatomical image in the training set into a plurality of regions; (b) computer readable program code generating, for each annotated, anatomical image in the training set, a hierarchy that includes a plurality of levels, each level in the hierarchy corresponding to one of the plurality of regions; (c) computer readable program code obtaining, from storage, at least one previously derived annotation for each level in the hierarchy and training a plurality of first classifiers to approximate the previously derived annotations, wherein the first classifiers are trained in a particular sequence such that the output of one of the first classifiers becomes input to another one of the first classifiers; (d) computer readable program code storing the trained, first classifiers of (c); and (e) computer readable program code locating an anatomical structure in the image of interest to the user based on stored trained, first classifiers.

In yet another embodiment, the present invention provides an article of manufacture comprising a non-transitory computer storage medium storing computer readable program code which, when executed by a computer, implements a computer-based medical image segmentation method for locating an anatomical structure in an image of interest to a user, using a training set of one or more anatomical images, the method comprising: (a) computer readable program code decomposing each anatomical image in the training set into a plurality of regions; (b) computer readable program code generating, for each anatomical image in the training set, a hierarchy that includes a plurality of levels, each level in the hierarchy corresponding to one of the plurality of regions; (c) computer readable program code training, for each anatomical image in the training set, a plurality of first classifiers to approximate one or more annotations, and storing one or more such estimated annotations by the first classifiers as previously derived annotations; (d) computer readable program code training a plurality of second classifiers to approximate the previously derived annotations, where the second classifiers are trained in a particular sequence such that the output of one of the second classifiers becomes an input to another one of the second classifiers; (e) computer readable program code outputting trained, second classifiers in (d); and (f) computer readable program code locating an anatomical structure in the image of interest to the user based on stored trained, second classifiers.

BRIEF DESCRIPTION OF THE DRAWINGS

The present disclosure, in accordance with one or more various examples, is described in detail with reference to the following figures. The drawings are provided for purposes of illustration only and merely depict examples of the disclosure. These drawings are provided to facilitate the reader's understanding of the disclosure and should not be considered limiting of the breadth, scope, or applicability of the disclosure. It should be noted that for clarity and ease of illustration these drawings are not necessarily made to scale.

FIG. 1A depicts an outline of a preferred path sequential learning algorithm.

FIG. 1H illustrates the flow chart for generating predicted segmentation, in step 5 of the algorithm of FIG. 1A, for a training image from cross validation at iteration t.

FIG. 1I illustrates how classifier $C^{T+1}$ is trained using as inputs, the outputs of FIG. 1H, the training images $I_1$ through $I_n$ and ground truth segmentations $L_1$ through $L_n$.

FIG. 2(a) depicts a graph of the average mutual information between feature images for the various segmentation protocols. FIG. 2(b) depicts a graph of the prediction accuracy (measured in Dice coefficient) for the various segmentation protocols. FIG. 2(c) depicts a graph of the prediction uncertainty for various segmentation protocols.

FIG. 5 depicts a table showing segmentation performance produced in the 4-fold cross-validation experiment for each anatomical region by joint label fusion, Auto-context, Stacked, and Path after 10 iterations.

FIG. 7 depicts a table outlining the segmentation performance produced for the 23 testing subjects by Auto-context, Stacked, and Path after 10 iterations on the 4-fold cross-validation experiment.

DESCRIPTION OF THE PREFERRED EMBODIMENTS

Figure 1B:
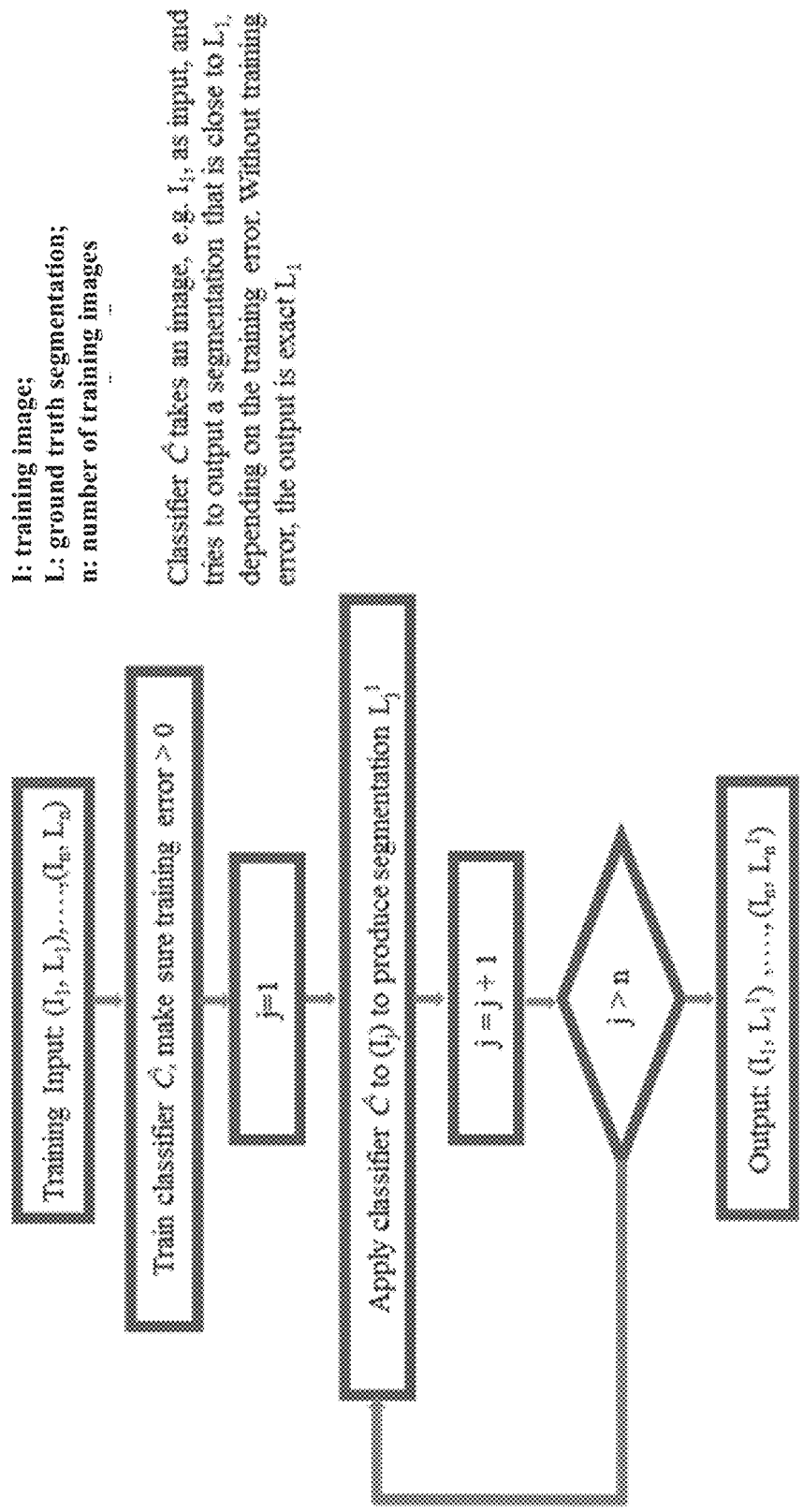
FIG. 1B depicts a flow chart outlining, at iteration 1, how step 3 of the algorithm of FIG. 1A generates a simplified segmentation problem.

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

Note that in this description, references to "one embodiment" or "an embodiment" mean that the feature being referred to is included in at least one embodiment of the invention. Further, separate references to "one embodiment" in this description do not necessarily refer to the same embodiment; however, neither are such embodiments mutually exclusive, unless so stated and except as will be readily apparent to those of ordinary skill in the art. Thus, the present invention can include any variety of combinations and/or integrations of the embodiments described herein.

Medical image segmentation is the problem of locating anatomical structures from medical images. The gold standard of segmentation is typically based on manual segmentation protocols. For automatic segmentation, classification-based machine learning techniques have been widely applied for medical image segmentation (see, for example, the paper to Tu et al. titled "Automated Extraction of the Cortical Sulci Based on a Supervised Learning Approach," IEEE TMI, 26(4), 2007, pp. 541-552). Given pre-labeled training images and pre-selected feature descriptors, one can directly train classifiers, e.g., AdaBoost or random forest, to discriminate different tissue classes based on extracted training samples.

The recent work on auto-context learning (see paper to Tu et al. titled "Auto-Context and Its Application to High-Level Vision Tasks and 3D Brain Image Segmentation," IEEE Trans. on PAMI, 32(10), 2010, pp. 1744-1757) and stacked hierarchical learning (see paper to Munoz et al. titled "Stacked Hierarchical Labeling," Computer Vision-ECCV 2010, Springer, 2010, pp. 57-70) applies a sequential learning strategy, where the output of an intermediate classifier is applied as contextual features for its subsequent classifier. The advantage of this strategy is that it propagates and integrates local image features, such that long-range structural context can be more effectively captured for semantic segmentation. One contribution is to show that these sequential learning methods can be interpreted as an approximation technique derived from a Bayesian formulation. To ensure that the approximation is accurate, a strong motivation is provided for an intuitive strategy that solves a difficult segmentation problem by breaking it into a series of simplified segmentation problems, i.e., problems that can be solved with less ambiguity than the original segmentation problem, and then solving them sequentially. If each simplified segmentation problem is interpreted as a step towards solving the original segmentation problem, then the series of simplified problems define a path. Sequentially teaching classifiers to solve each simplified problem along the path leads to a more effective way for solving the original segmentation problem.

Another contribution as per the teachings of the present invention is a learning-based method for automatically deriving simplified segmentation problems. In a related work (see paper to Munoz et al. titled "Stacked Hierarchical Labeling," Computer Vision-ECCV 2010, Springer, 2010, pp. 57-70), simplified segmentation problems are built through a coarse-to-fine hierarchical decomposition of regions for images using low level segmentation. However, this method does not address the complexities in learning models for solving these problems. Hence, there is no guarantee that the generated hierarchical segmentation problems can be more easily solved than the original problem. This limitation is addressed in this disclosure by explicitly controlling the complexities of classifiers taught for modeling the simplified segmentation problem.

The present invention's method was applied on the canine leg muscle segmentation dataset from the SATA segmentation challenge (see paper to Asman et al. titled "MICCAI 2013 Segmentation Algorithms, Theory and Applications (SATA) Challenge Results Summary," MICCAI 2013 Challenge Workshop on Segmentation: Algorithms, Theory and Applications, Springer, 2013), and it is noted that the present invention's technique produced significant improvement over the auto-context technique and significantly improved the state of the art performance on the challenge category using standard registration.

Method

A Probabilistic View for Image Segmentation

Image segmentation can be formulated as a conditional probability estimation problem p(S|I), where I is an observed image and S is a segmentation for I. Given a target segmentation protocol and training images, for which the gold standard segmentation has been produced following the protocol, automatic segmentation can be achieved by estimating the conditional probability p(S|I) through classification techniques. A common technique directly estimates the posterior probability of assigning label l to a location x in I based on image features, i.e., p(l|I, x). Under a conditional independent assumption, the problem can be addressed by p(l|I, x)=p(l|I(N(x))) and p(S|I)=$\Pi_x$p(S(x)|I(N(x))), where N(x) is a neighborhood surrounding x and I(N(x)) is the image features extracted from the neighborhood. Given the estimated probabilities, the maximum a posterior (MAP) segmentation can be derived as S(x)=arg $\max_l$p(l|I(N(x))).

Complexity of Image Segmentation

Under the probabilistic view, each segmentation problem can be modeled by classifiers that learn from training data. Hence, the complexity of a segmentation problem can be measured by the complexity of the corresponding classification problem. The complexity of a segmentation problem is defined as follows:

$$H(D)=H(D;C)+H(D|C) \quad (1)$$

where D=(F,Y) are data extracted from training images with F={$f_1$, ..., $f_n$} specifying feature representations of n samples and Y={$y_1$, ..., $y_n$} specifying the segmentation labels. C is a classifier. H(D;C) is the information about the segmentation problem captured by C. H(D|C) is the residual information not captured by classifier C, which can be defined as:

$$H(D|C) = \frac{1}{n}\sum_{i=1}^{n} -\log p(y_i | f_i, C) \quad (2)$$

where p($y_i$|$f_i$, C) is the label posterior computed by C using feature $f_i$.

In the literature, classifier complexity H(C) is often described as the complexity of decision boundaries. Many factors may affect classifier complexity. The most influential factors include features and the learning model, e.g., linear or nonlinear. When a classifier accurately models a classification problem, H(D)=H(D;C)=H(C). Due to overfitting, it is common that H(D;C)<H(C) and H(D|C)>0. When overfitting is minimized, e.g., through techniques such as cross-validation, the complexities of two segmentation problems can be approximately compared by the residual terms, given that the modeling classifiers for the two problems have similar complexities, e.g., both trained by the same learning model using same image features. If p(l|f,C) is narrowly peaked around its maximum for each data, there is little residual information. In contrast, if the distribution is flat or multiple modes are widely scattered, the segmentation problem is more complex as more residual information is not captured by C.

Bayesian Approximation

Under the Bayesian rule, the posterior label probability distribution of a target segmentation can be computed as:

$$p(l|I,x)=\int_{S'} p(S'|I,C^1)p(l|I,S',x) \quad (3)$$

S' index through all possible segmentations for I. p(S'|I,$C^1$) is the probability of a segmentation given the observed image I as modeled by classifier $C^1$.

Although it is intractable to enumerate all feasible segmentations in (3), accurate approximation exists when certain conditions are satisfied. When p(S"|I,$C^1$) is narrowly peaked around its maximum, a commonly applied approximation is based on the MAP segmentation (e.g., see paper to Leemput et al. titled "Automated Segmentation of Hippocampal Subfields From Ultra-High Resolution In Vivo MRI," Hippocampus, v19, 2009, pp. 549-557):

$$p(l|I,x) \sim p(S^1|I,C^1)p(l|I,S^1,x) \propto p(l|I,S^1,x) \quad (4),$$

where $S^1$ is the MAP segmentation derived from $C^1$. The condition also means that the underlying segmentation problem modeled by $C^1$ can be reliably solved by $C^1$. If the condition is not satisfied, the MAP solution has larger variations, which results in greater mismatch between features extracted from $S^1$ during training and testing. This limitation makes learning more easily prone to overfitting, reducing the benefit of adding $S^1$ as additional features. Since p($S^1$|I,$C^1$) is a constant scale factor, to solve the original segmentation problem, only p(l|I,$S^1$,x) needs to be estimated. As shown in the paper to Tu et al. titled "Auto-Context and Its Application to High-Level Vision Tasks and 3D Brain Image Segmentation," IEEE Trans. on PAMI, 32(10), 2010, pp. 1744-1757, the paper to Wang et al. titled "A Learning-Based Wrapper Method to Correct Systematic Errors in Automatic Image Segmentation: Consistently Improved Performance in Hippocampus, Cortex and Brain," Neuroimage, 55(3), 2011, pp. 968-985, and the paper to Montillo et al. titled "Entangled Decision Forests and Their Application for Semantic Segmentation of CT Images," Information Processing in Medical Imaging, Springer, 2011, pp. 184-196, when $S^1$ is correlated with the target segmentation, it provides contextual information, such as shape or spatial relations between neighboring anatomical regions, that is not captured by local image features.

The above approximation has an intuitive interpretation. A segmentation problem may be solved through transferring it into a simpler segmentation problem that can be solved with less ambiguity. Solving the simplified segmentation problem first may help solving the original segmentation problem.

A Case Study:

Corrective learning (see the paper to Wang et al. titled "A Learning-Based Wrapper Method to Correct Systematic Errors in Automatic Image Segmentation: Consistently Improved Performance in Hippocampus, Cortex and Brain," Neuroimage, 55(3), 2011, pp. 968-985) applies classification techniques to correct systematic errors produced by a host segmentation method with respect to some gold standard segmentation. In one non-limiting context, the segmentation produced by the host method is a MAP solution. In corrective learning, the classifiers trained for making corrections aim to estimate label posteriors given the observation of the image and the segmentation produced by the host method, i.e., p(l|I,$S^1$,x). Hence, corrective learning is in fact an application of the MAP approximation (4). The fact that corrective learning achieves better performance than learning purely based on image features on some previous studies indicates the effectiveness of the MAP-based approximation. It is noted that corrective learning may work even more effectively when the host method aims to solve a simplified segmentation problem derived from the target segmentation problem.

Iterative Extension: Finding a Path to Segmentation

The approximation in (4) can be recursively expanded as follows:

$$p(l|I,x) \sim p(S^1|I,C^1)p(l|I,S^1,x) \quad (5)$$

$$\sim p(S^1|I,C^1)p(S^2|I,S^1,C^2)p(l|I,S^1,S^2,x) \quad (6)$$

$$\sim p(S^1|I,C^1) \ldots p^n(S^n|I,S^1,\ldots,S^{n-1},C^n)p(l|I,S^1,\ldots,S^n,x) \quad (7)$$

$$\propto p(l|I,S^1,\ldots,S^x) \quad (8)$$

$C^i$ are trained classifiers and $S^i$ is the MAP solution derived from $C^i$.

For this approximation to be accurate, a necessary condition is that for each $1 < i \leq n$, $S^i$ can be computed with little ambiguity with $C^i$ given the image I and the MAP segmentations obtained from previous iterations, i.e., $\{S^1, \ldots, S^{i-1}\}$. For the original segmentation problem to benefit from this approximation, an additional requirement is that each $S^i$ must provide additional information about the desired segmentation that is not already captured by I and $\{S^1, \ldots, S^{i-1}\}$. In other words, $S^i$ should be more similar to the desired segmentation as i increases. Under these requirements, $(C^1, \ldots, C^n)$ defines a path for solving the original segmentation problem. Each $C^i$ aims to accurately solve a simplified segmentation problem. As i increases, the complexity of the problem solved by $C^i$ also increases.

The Path learning algorithm

To implement the sequential learning model in the paper to Munoz et al. titled "Stacked Hierarchical Labeling," Computer Vision-ECCV 2010, Springer, 2010, pp. 57-70, an iterative extension to the corrective learning method is proposed (see the paper to Wang et al. titled "A Learning-Based Wrapper Method to Correct Systematic Errors in Automatic Image Segmentation: Consistently Improved Performance in Hippocampus, Cortex and Brain," Neuroimage, 55(3), 2011, pp. 968-985). The motivation for building the implementation based on corrective learning is that corrective learning is designed to be more effective in utilizing segmentation results produced in previous iterations for building stronger segmentation classifiers.

FIG. 1A depicts an outline of a preferred path sequential learning algorithm. This is an iterative algorithm for training sequential classifiers for image segmentation, using training images. At each iteration, the algorithm repeatedly works on three subtasks: 1) generating a simplified segmentation problem, based on training images and the intermediate segmentation results produced for training images from previous iterations, and then 2) solving the simplified segmentation problem by training a segmentation classifier, and finally 3) preparing for the next iteration by generating intermediately predicted segmentations for the training images using cross-validation.

Figure 1C:
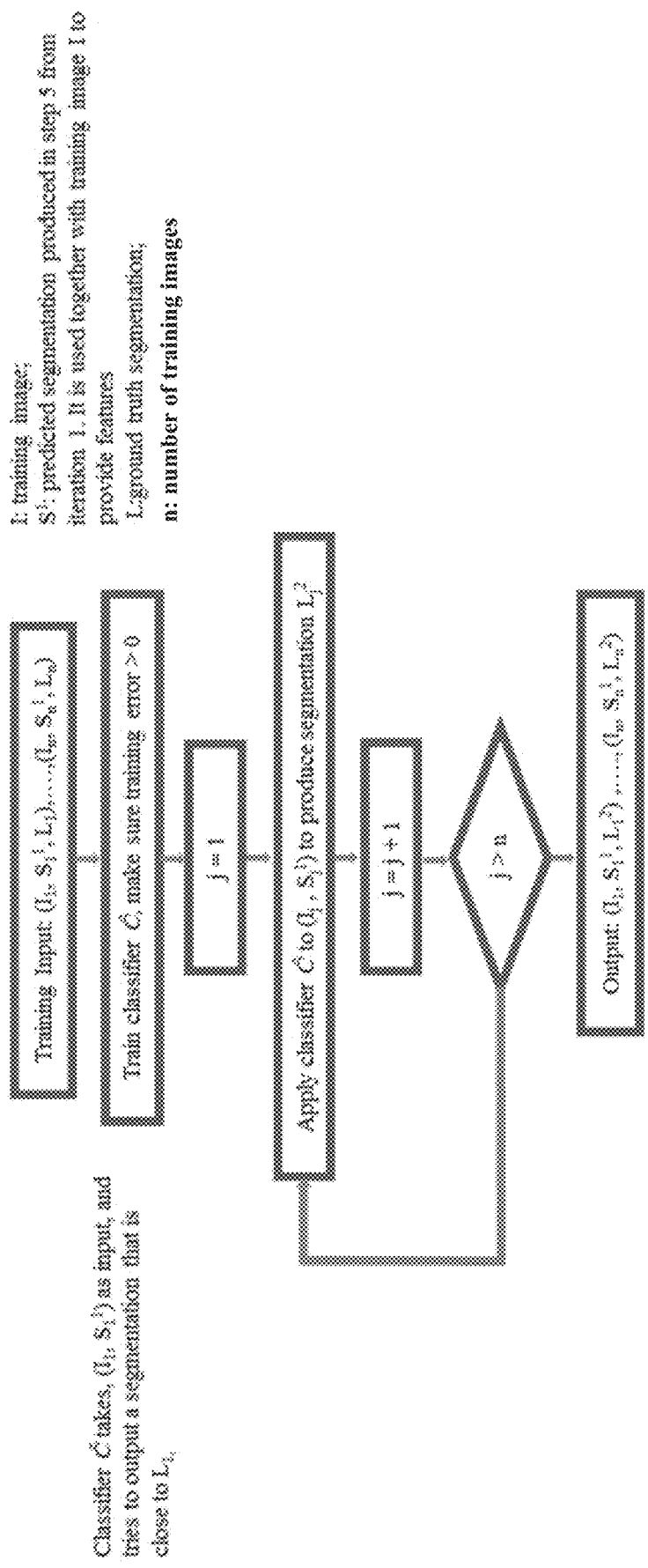
FIG. 1C depicts a flow chart outlining, at iteration 2, how step 3 of the algorithm of FIG. 1A generates the simplified segmentation problem.
Figure 1D:
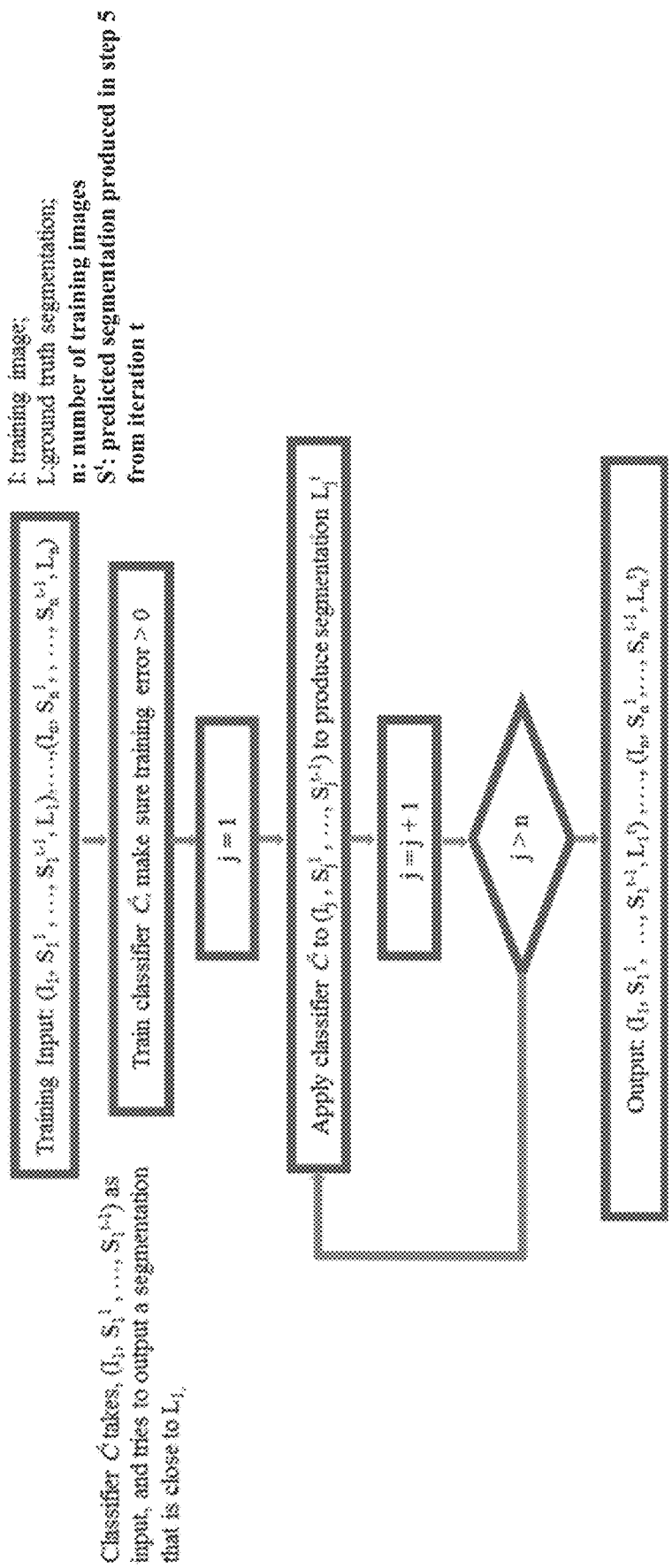
FIG. 1D depicts a flow chart outlining, at iteration t, how step 3 of the algorithm of FIG. 1A generates the simplified segmentation problem.

FIG. 1B depicts a flow chart outlining, at iteration 1, how step 3 of the algorithm of FIG. 1A generates a simplified segmentation problem. In FIG. 1B, n training images $I_1$ through $I_n$ are input along with their corresponding ground truth segmentations $L_1$ through $L_n$, where classifier $\hat{C}$ takes an image, e.g., $I_1$, as input, and tries to output a segmentation, e.g., $L_1^1$, that is close to $L_1$, depending on the training error (without training error, the output is exact $L_1$). The following is output at the end of step 3 in the first iteration: $(I_1, L_1^1), \ldots, (I_n, L_n^1)$. FIG. 1C depicts a flow chart outlining, at iteration 2, how step 3 of the algorithm of FIG. 1A generates the simplified segmentation problem. In iteration 2 of FIG. 1C, in addition to the n training images $I_1$ through $I_n$ and their corresponding ground truth segmentations $L_1$ through $L_n$, predicted segmentation $S_1^1$ through $S_n^1$ are also input, where the temporary classifier $\hat{C}$ takes an image, e.g., $I_1$ and $S_1^1$, as input, and tries to output a segmentation, e.g., $L_1^2$, that is close to $L_1$. Predicted segmentation $S_1^1$ through $S_n^1$ are computed using cross validation as per the flow chart depicted in FIG. 1F, where the output from the first iteration in FIG. 1B, i.e., $(I_1, L_1^1), \ldots, (I_n, L_n^1)$, is used as the input. In iteration t of FIG. 1D, in addition to the n training images $I_1$ through $I_n$ and their corresponding ground truth segmentations $L_1$ through $L_n$, predicted segmentation $S_1^{t-1}$ through $S_n^{t-1}$ are also input, where the classifier $\hat{C}$ takes an image, e.g., $I_1, S_1^1, \ldots, S_1^{t-1}$, as input, and tries to output a segmentation, e.g., $L_1^{t-1}$, that is close to $L_1$. Predicted segmentation $S_1^{t-1}$ through $S_n^{t-1}$ are computed using cross validation as per the flow chart depicted in FIG. 1G, where the output from the $t-1^{th}$ iteration, i.e., $(I_1, L_1^{t-1}), \ldots, (I_n, L_n^{t-1})$, is used as the input along with previous predicted segmentations $S_1^{t-2}$ through $S_n^{t-2}$. In FIG. 1G, classifier $c_j$ is applied to $(I_j, S_j^1, \ldots, S_j^{t-2})$ to produce segmentation $S_j^{t-1}$". As a point of distinction, it should be noted that $C^1, C^2, \ldots, C^T, C^{T+1}$ are the output of FIG. 1A, while $c_1$ through $c_n$ are temporary classifiers and they are not saved after each time step 5 in FIG. 1F is finished.

Figure 1E:
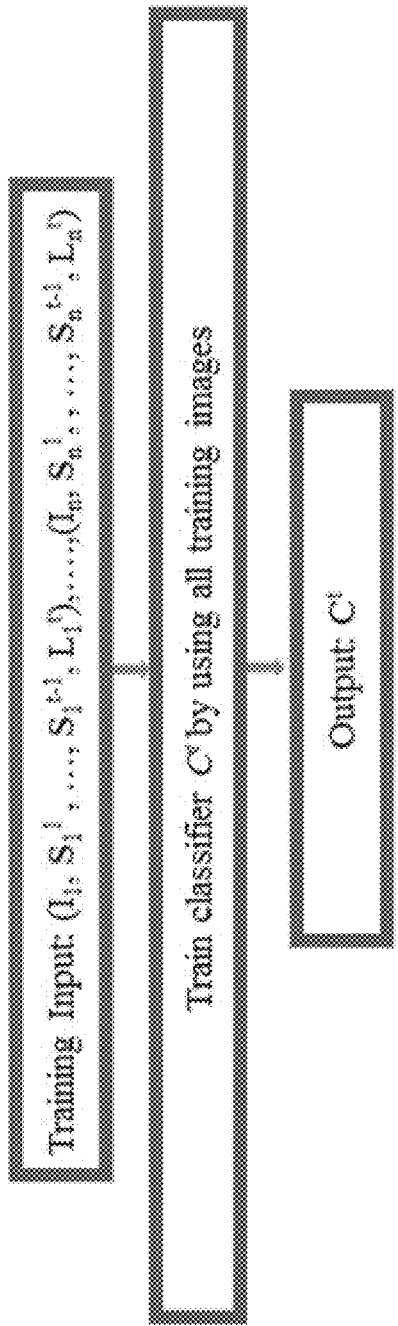
FIG. 1E illustrates the flow chart of how the output in step 4 of the algorithm of FIG. 1A is calculated by training classifiers.
Figure 1F:
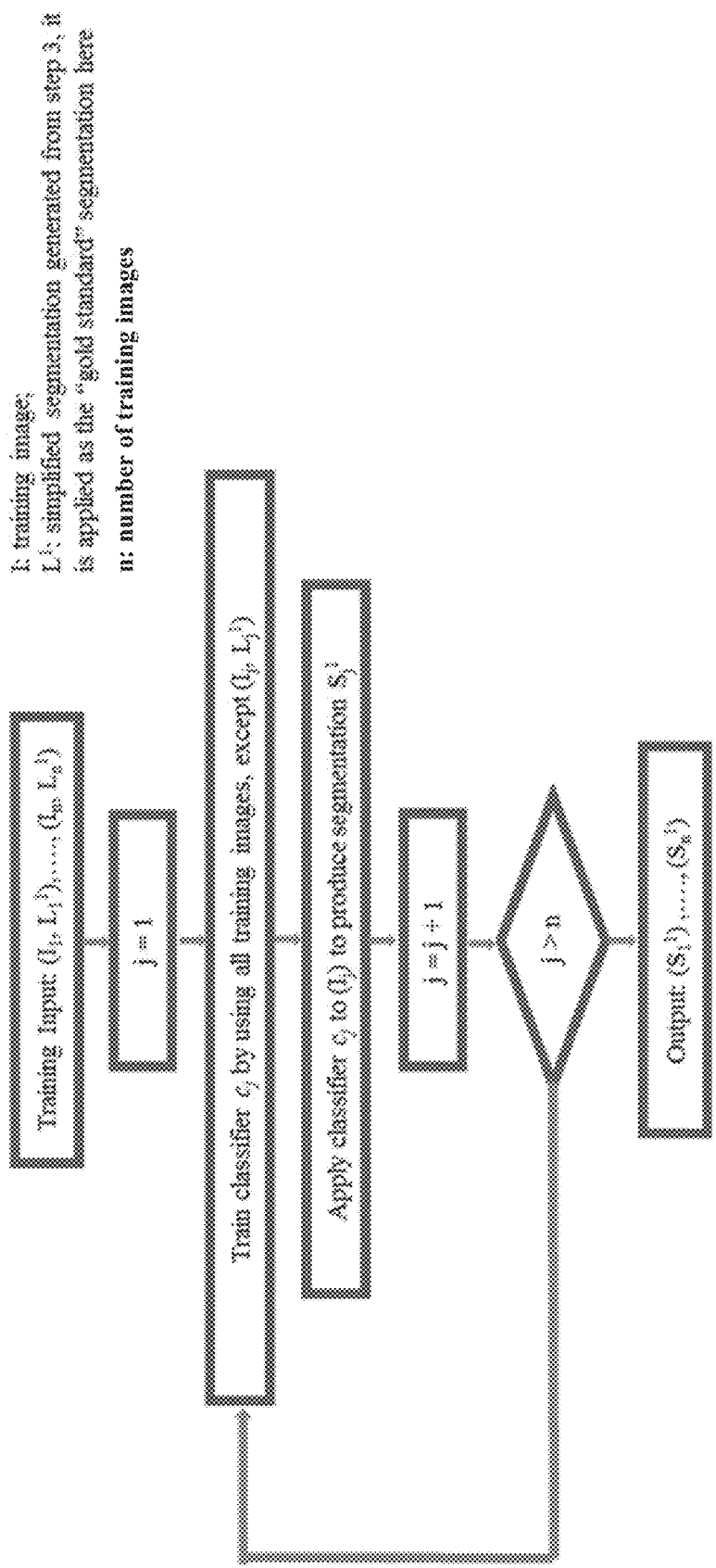
FIG. 1F illustrates the flow chart for generating predicted segmentation, in step 5 of the algorithm of FIG. 1A, for a training image from cross validation.
Figure 1G:
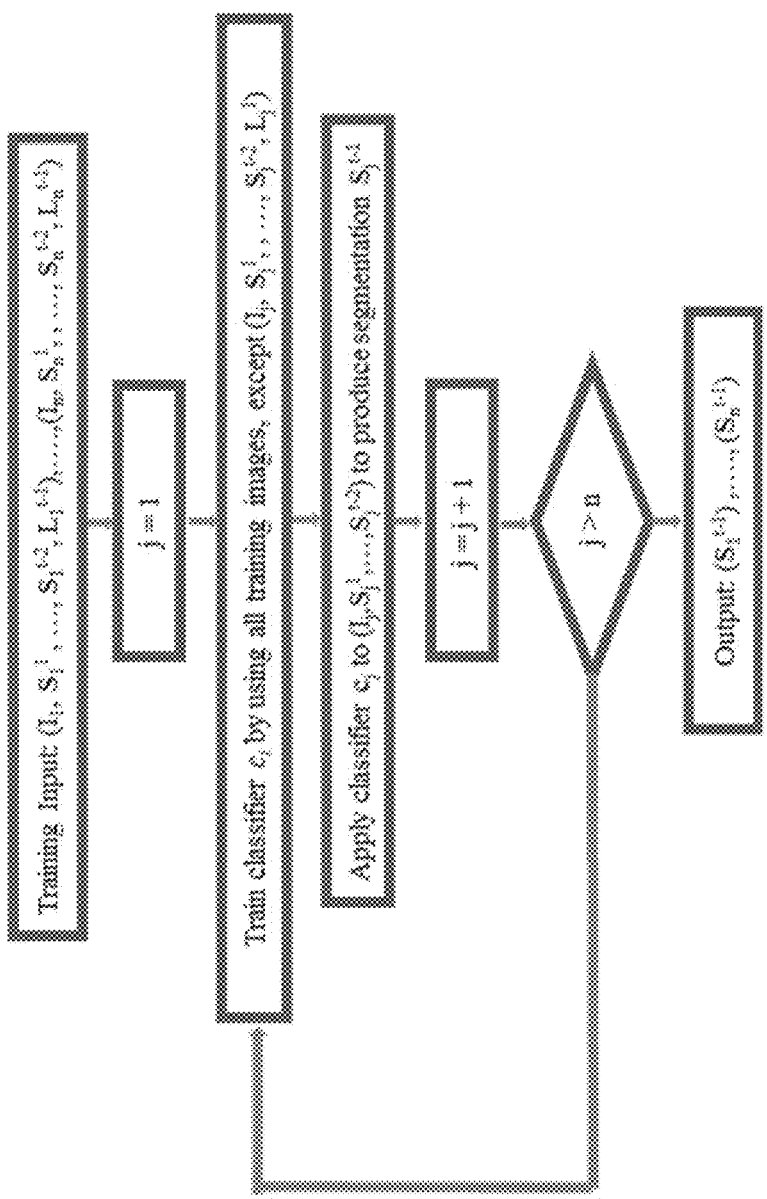
FIG. 1G illustrates the flow chart for generating predicted segmentation, in step 5 of the algorithm of FIG. 1A, for a training image from cross validation at iteration t−1.
Figure 11:
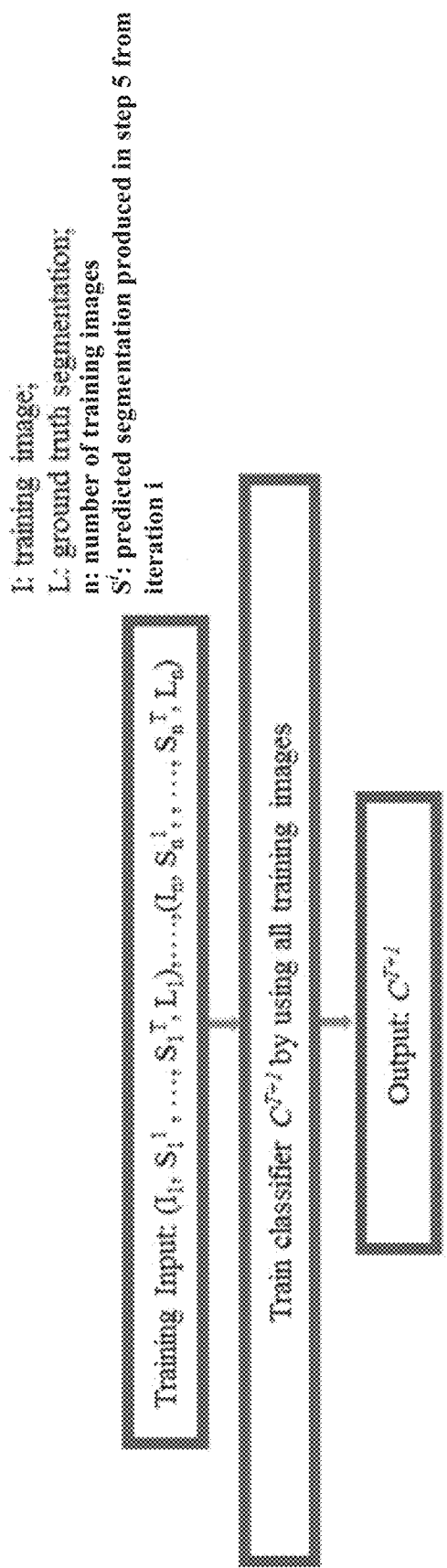

FIG. 1E illustrates the flow chart of how the output in step 4 of the algorithm of FIG. 1A is calculated by training classifiers $C^t$ using inputs $(I_1, S_1^1, \ldots, S_1^{t-1}, L_1^t), \ldots, (I_n, S_n^1, \ldots, S_n^{t-1}, L_n^t)$, where trained classifier $C^t$ is output.

FIG. 1H illustrates how predicted segmentations $S_1^t$ through $S_n^t$ are computed using cross validation, where the output from the $t-1^{th}$ iteration, i.e., $(I_1, L_1^t), \ldots, (I_n, L_n^t)$, is used as the input along with previous predicted segmentations $S_1^{t-1}$ through $S_n^{t-1}$. In FIG. 1H, classifier $c_j$ is applied to $(I_j, S_j^1, \ldots, S_j^{t-1})$ to produce segmentation $S_j^{t}$".

FIG. 1I illustrates how classifier $C^{T+1}$ is trained using as inputs, the outputs of FIG. 1H (i.e., $S_1^t$ through $S_n^t$), the training images $I_1$ through $I_n$ and ground truth segmentations $L_1$ through $L_n$, where trained classifier $C^{T+1}$ is output.

Figure 1J:
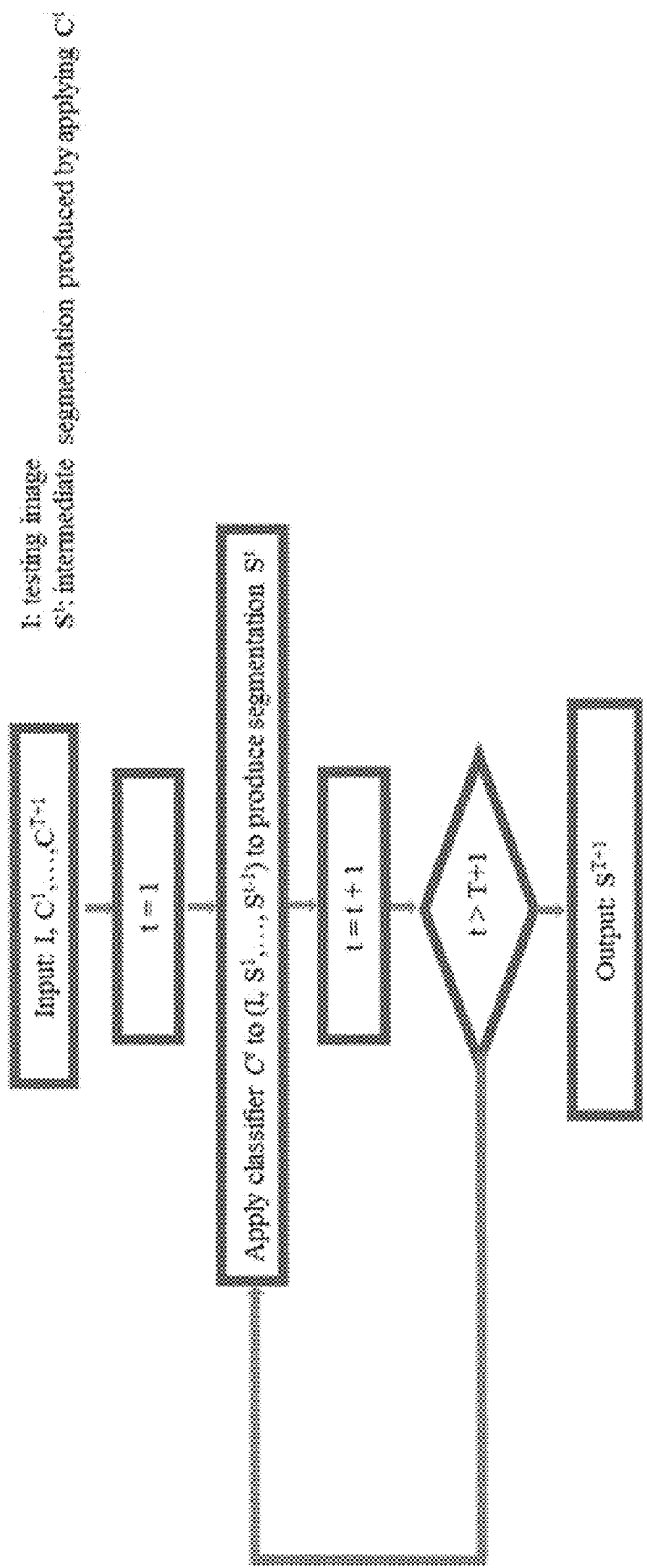
FIG. 1J depicts how the output classifiers $C^1$ through $C^{T+1}$ are input along with the testing image I to produce segmentation of the testing image.

FIG. 1J depicts how the output classifiers $C^1$ through $C^{T+1}$ are input along with the testing image I to produce segmentation of the testing image. This process is iteratively implemented from t=1 through t=T+1 with segmentation $S^{T+1}$ output as the final segmentation of the testing image.

For step 4 at each iteration t, AdaBoost classifiers (see paper to Freund et al. titled "A Decision-Theoretic Generalization of On-Line Learning and an Application to Boosting," Proceedings of the $2^{nd}$ European Conf. on Computational Learning Theory, 1995, pp. 23-27) are trained to solve the simplified segmentation. First, a working region of interest (ROI) is defined for each label by performing dilation to the set of all voxels assigned the label in the MAP segmentation produced in the previous iteration, i.e., $S^{t-1}$. Using instances uniformly sampled within a label's working ROI, one AdaBoost classifier is trained to identify voxels assigned to this label against voxels assigned to other labels in the target segmentation within the ROI. To apply these classifiers on a testing image, each classifier is applied to evaluate the confidence of assigning the corresponding label to each voxel within the label's working ROI. If a voxel belongs to the ROI of multiple labels, the label whose classifier gives the maximal posterior at the voxel is chosen for the voxel. At the first iteration, if no segmentation has been produced yet, the AdaBoost classifiers are trained without using working ROIs.

Three types of features are applied to describe each voxel, including spatial, appearance, and contextual features. The spatial features are computed as the relative coordinate of each voxel to the ROI's center of mass. The appearance features are derived from the voxel's neighborhood patch from the training image(s). The contextual features are extracted from the voxel's neighborhood patch from all MAP segmentations and spatial label probability maps produced in previous iterations. To enhance spatial correlation, the joint spatial-appearance and joint spatial-contextual features are also included by multiplying each spatial feature with each appearance and contextual feature, respectively. If no segmentation has been produced yet, only the appearance features will be applied.

Stacking Learning:

Another issue to address is that sequential learning is more prone to the overfitting problem. Due to overfitting, the intermediate segmentation results produced for a testing image may be different from those produced for training images. Since these segmentation results are applied as features in subsequent iterations, this training/testing mismatch will compromise the performance of the classifiers that learn in subsequent iterations. To alleviate this problem, the stacking technique (see paper to D. H. Wolpert titled "Stacked Generalization," Neural Networks, 5(2), 1992, pp. 241-259, the paper to Cohen et al. titled "Stacked Sequential Learning," Proceedings of the IJCAI, Morgan Kaufmann Publishers Inc., 2005, pp. 671-676 and the paper to Munoz et al. titled "Stacked Hierarchical Labeling," Computer Vision-ECCV 2010, Springer, 2010, pp. 57-70) may be applied (at step 5 in the above algorithm). For training, the MAP segmentation produced for each training image is produced from cross-validation.

Relation to Auto-Context Learning:

A key difference from the auto-context technique is that the present invention's technique reduces the approximation error by predicting a simplified segmentation problem at each iteration, while auto-context always tries to predict the original segmentation problem. The other difference is that auto-context does not apply the Stacking technique. Both improvements allow the present invention's method to retain performance gains through more iterations.

Figure 1K:
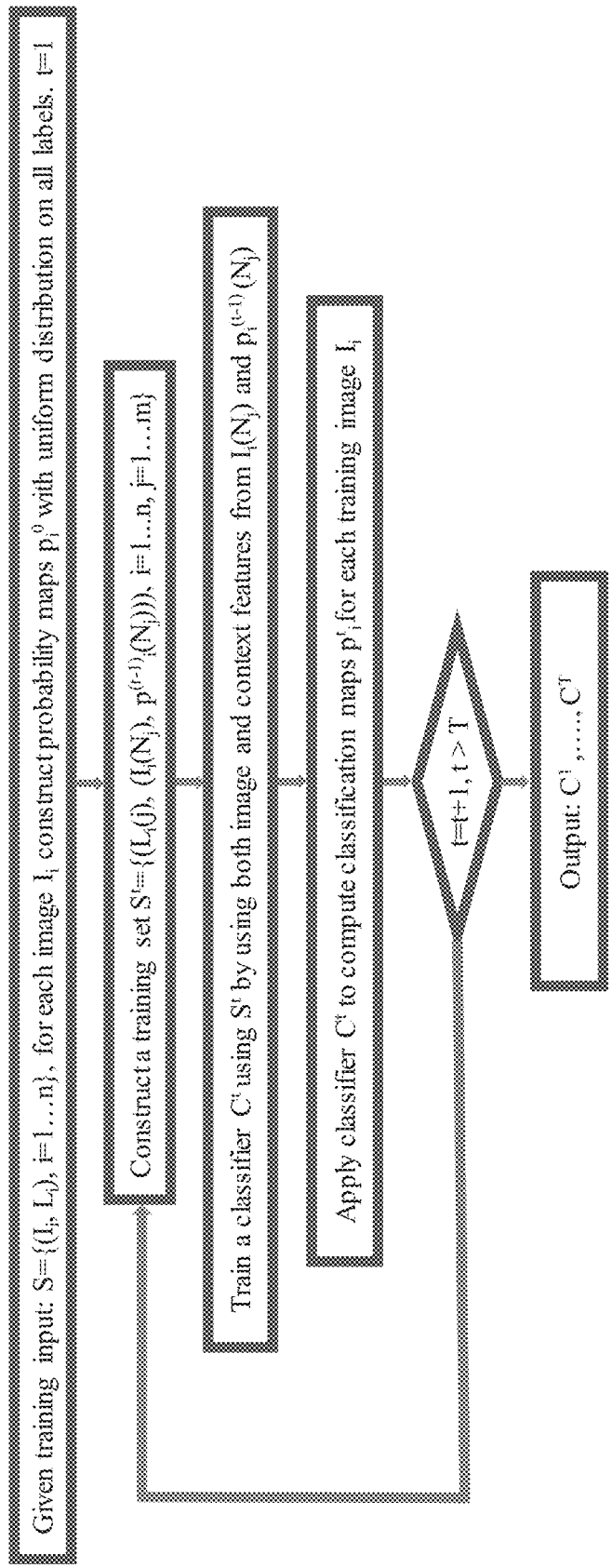
FIGS. 1K-L are provided to further help understand the difference between the auto-context learning algorithm and the present invention's path sequential algorithm.
Figure 1L:
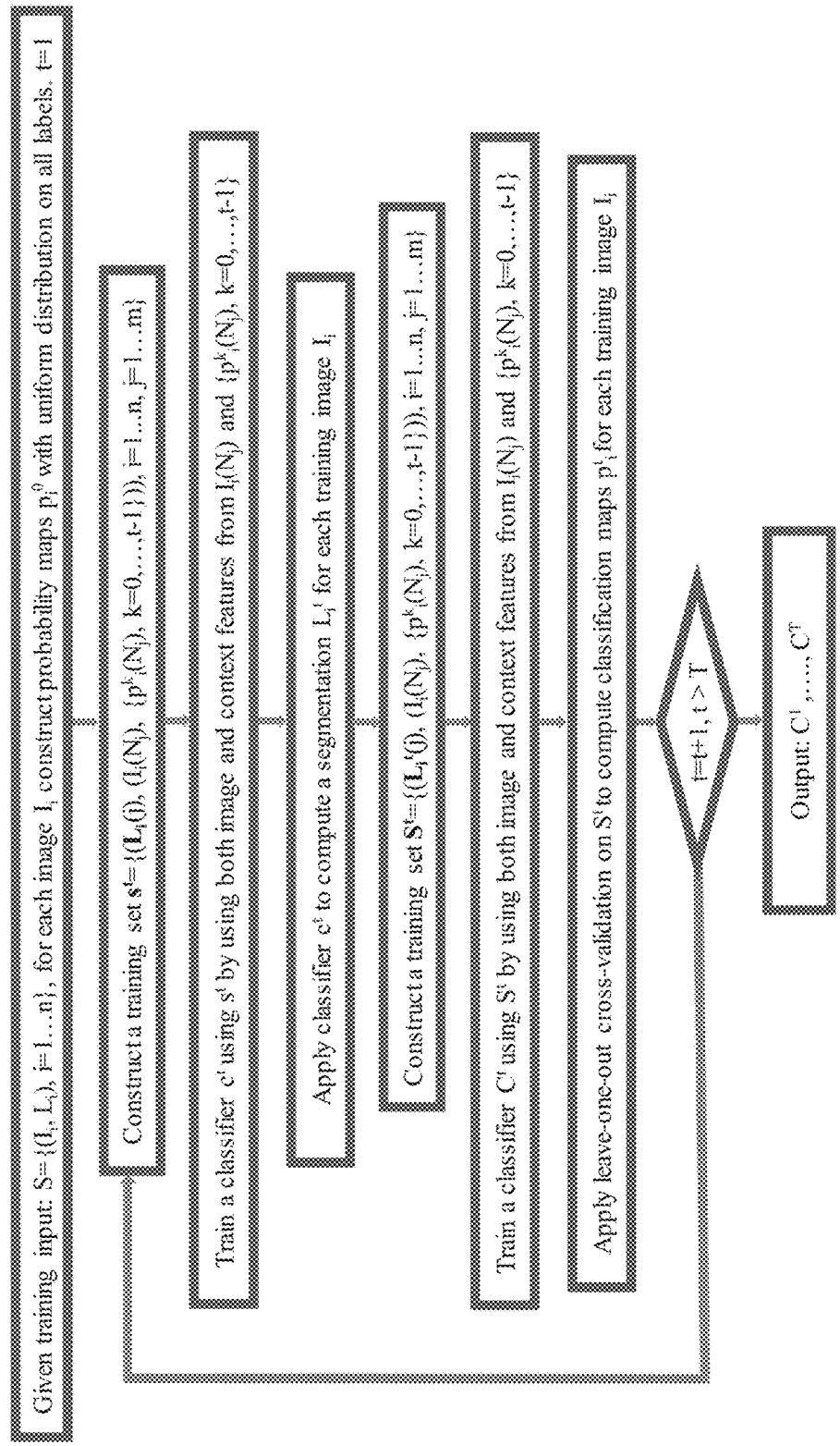

FIGS. 1K-L are provided to further help understand the difference between the auto-context learning algorithm and the present invention's path sequential algorithm. There are three key difference between the two algorithms.

First, the sequence of classifiers produced by auto-context learning are trained based on the original ground truth segmentations of the training images, i.e., $\{L_i, i=1, \ldots, n\}$, while the resulting classifiers produced by the Path algorithm are trained based on transformed segmentations produced for the training images at each iteration, i.e., $\{L_i^t, i=1, \ldots, n\}$. The transformed segmentations can be more accurately predicted than the original ground truth segmentation. By training classifiers to solve the transformed segmentations, the Path algorithm reduces the risk of overfitting on each produced classifier.

Second, the contextual features employed by auto-context learning at each iteration are extracted from the classification maps produced for the training images at a single iteration right before the current iteration. In contrast, the contextual features employed by the Path algorithm at each iteration are extracted from the classification maps produced for the training images from all previous iterations.

Third, auto-context learning produces the classification maps for each training image at each iteration directly based on the classifier produced at that iteration. In contrast, the Path algorithm applies a leave-one-out cross-validation strategy to produce classification maps for each training image. That is for each training image, one classifier is trained by using the remaining training images and is then applied to produce the classification maps for the target training image.

These three differences are designed to reduce the risk of overfitting and improve the overall effectiveness of sequential learning.

Generating Simplified Segmentation Problems

A crucial requirement for the above algorithm is the ability to define simplified segmentation problems for any given segmentation problem. For this task, a learning-based approach is invoked.

The paper to Munoz et al. titled "Stacked Hierarchical Labeling," Computer Vision-ECCV 2010, Springer, 2010, pp. 57-70, proposed to break a segmentation problem into stacked hierarchical segmentation problems. Given an image, a coarse-to-fine hierarchical decomposition of regions for the image is first created using low level segmentation methods. For each decomposition of regions in the hierarchy, a new probabilistic segmentation problem is created by generating label distributions for each region according to the original segmentation. With the hierarchical representation, the stacked hierarchical segmentation problem is solved by sequentially solving the coarse-to-fine segmentation problems. The results produced at each level are passed as contextual features to assist solving the next finer level segmentation problem. This approach has one key limitation. Since the problems at various hierarchical levels are defined based on low level segmentation, without considering the difficulty in learning models for predicting them, there is no guarantee that any coarser level probabilistic segmentation problem can be solved with less ambiguity than solving finer level segmentation problems or the original segmentation problem. Hence, the accuracy of applying (7) still may be compromised.

Simplified segmentation problems may be generated directly from learning by controlling the complexity of their modeling classifiers. In this disclosure, the AdaBoost classifier is applied. AdaBoost is an ensemble learning technique that iteratively builds a strong classifier from linearly combining complimentary weak classifiers (see paper to Freund et al. titled "A Decision-Theoretic Generalization of On-Line Learning and an Application to Boosting," Proceedings of the $2^{nd}$ European Conf. on Computational Learning Theory, 1995, pp. 23-27). Typically, as training iteration increases, training error decreases and the learned classifier can model more complex decision boundaries to better fit the training data. To generate simplified segmentation problems, given feature images and target segmentations, AdaBoost classifiers are trained (as described in section titled "The Path Learning Algorithm") to predict the target segmentation using all training images. When training errors are greater than zero, simplified segmentations can be generated by applying the trained classifiers to segment the training images. This approach works by setting the residual information to zero in (1)(2). By varying the iterations of AdaBoost training, the complexity of the simplified segmentation problem can be controlled as well.

By reducing the complexity of the modeling classifiers, it is ensured that the simplified segmentation problem can be more easily predicted than the original segmentation problem, making the MAP segmentation based approximations (4)(7) better conditioned. Furthermore, through AdaBoost training, the learned classifiers may encode non-linear contextual relations between the applied features into the simplified segmentation protocol, making the simplified segmentation problem useful for predicting the target segmentation.

FIG. 2(a) depicts a graph of the average mutual information between feature images and various segmentation protocols, including manual segmentation and simplified segmentation obtained with 100, 200, 300, 400, and 500 AdaBoost training iterations, respectively. FIG. 2(b) depicts a graph of the prediction accuracy (measured in Dice coefficient) for the various segmentation protocols. FIG. 2(c) depicts a graph of the prediction uncertainty for various segmentation protocols.

Empirical Justification:

To verify its effectiveness, an experimental study was conducted using the canine leg muscle data (described later). 22 training subjects were applied. For each subject, two MR images are available. The manual segmentation for seven muscle types are provided for each training subject. For each subject, an automatic segmentation produced by multi-atlas joint label fusion (see paper to Rohlfing et al. "C.R.M.: Quo Vadis Atlas-Based Segmentation?" The Handbook of Medical Image Analysis: Registration Models (Volume III), Springer, 2005, pp. 435-486, the paper to Heckemann et al. titled Automatic Anatomical Brain MRI Segmentation Combining Label Propagation and Decision Fusion," NeuroImage, v33, 2006, pp. 115-126, and the paper to Wang et al. titled "Multi-Atlas Segmentation with Joint Label Fusion," IEEE Trans. on PAMI, 35(3), 2013, pp. 611-623) is produced by using the remaining training subjects as atlases. In this disclosure, the corrective learning technique was applied to train AdaBoost classifiers for predicting manual segmentation using all training subjects, with both the MR images and the multi-atlas segmentation applied as feature images. To generate segmentations with various complexities, simplified segmentation for each training subject were produced using the AdaBoost classifiers trained with 100, 200, 300, 400, and 500 iterations, separately. Hence, five simplified segmentation problems were produced.

FIG. 2(a) shows the average mutual information measured between each of the feature images, i.e., two MR images and the multi-atlas segmentation, and each of the segmentation protocols, i.e., the manual segmentation and the five simplified segmentations, respectively. The feature images contain higher mutual information for simplified segmentations than for manual segmentation, indicating less uncertainty in predicting the simplified segmentation protocols using the feature images. As expected, since simplified segmentations produced using more AdaBoost training iterations are more similar to manual segmentation, the feature images also contain less mutual information for them.

To verify that predicting simplified segmentation problems indeed can be achieved with less uncertainty than predicting manual segmentation, a leave-one-out cross-validation experiment was conducted. For each training subject, the remaining training subjects were applied to train another set of AdaBoost classifiers using the feature images to predict the manual segmentation and each of the five simplified segmentations, respectively. FIG. 2(b) summarizes the segmentation performance. The simplified segmentation problems can be estimated with higher accuracy (~0.95 average Dice coefficient) than manual segmentation (~0.75 Dice coefficient). To quantify the uncertainty in predicting different segmentation problems, the following function was applied:

$$U(C, I) = \frac{\sum_x -\log(p(l(x)|I, x, C))}{N},$$

where l(x) is the MAP label derived by classifier C and N is the number of processed voxels in I. This function measures the averaged uncertainty over the image. When $p(l(x)|I,x,C))=1$ for every x, there is no uncertainty and the uncertainty measure is zero, otherwise the uncertainty measure is greater than zero. FIG. 2(c) shows the average uncertainty produced for each segmentation problem in the leave-one-out experiment.

Figure 3:
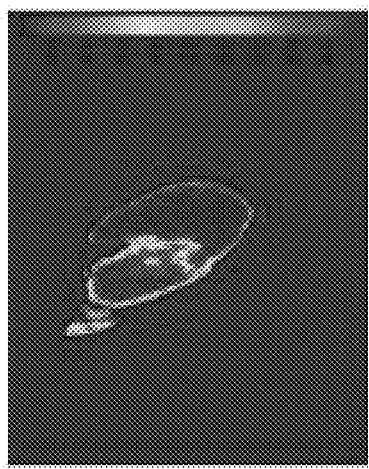
FIGS. 3(a)-(f) show examples of various probability maps.
Figure 3:
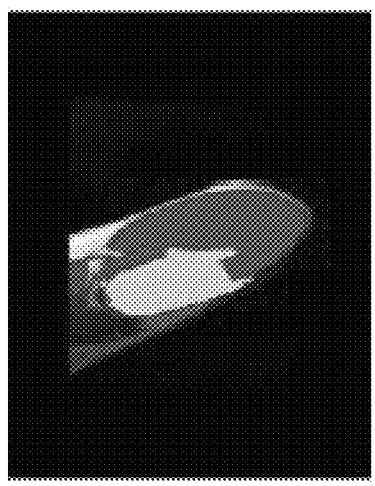
Figure 3:
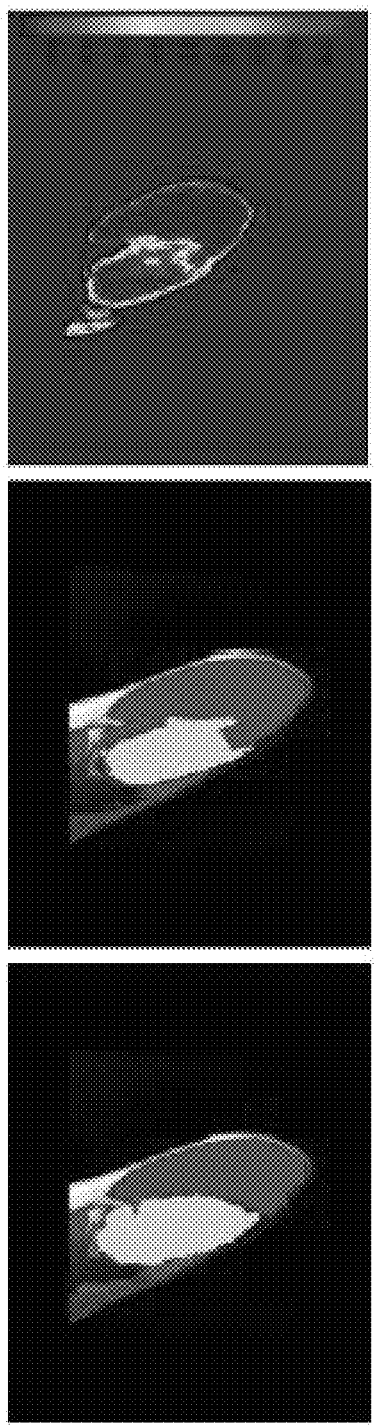
Figure 3:
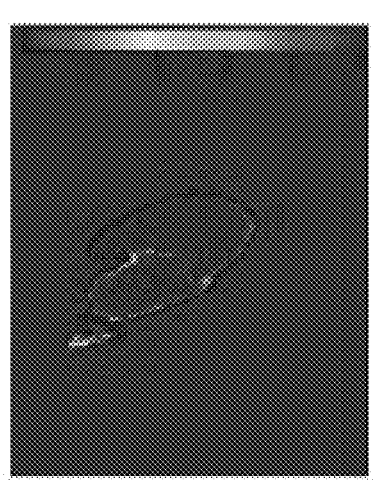
Figure 3:
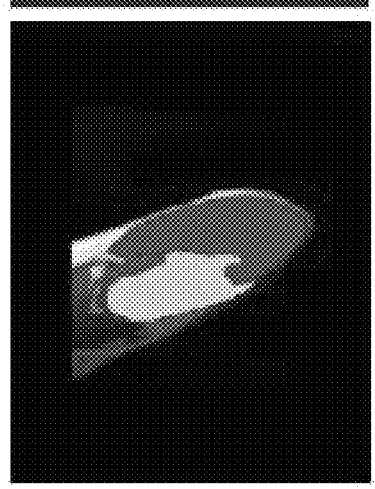
Figure 3:
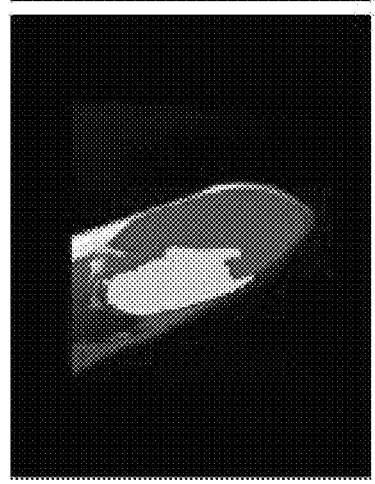

FIGS. 3(a)-(f) show one example of the MAP probability map, i.e. p(l(x)|I,x,C), produced for predicting manual segmentation and the simplified segmentation obtained using 500-iteration AdaBoost learning, respectively. Clearly, there is less uncertainty in predicting the simplified segmentation problem than predicting manual segmentation. FIG. 3(a) depicts a map based on the manual segmentation for one subject. FIG. 3(d) depicts a map based on the simplified segmentation produced by AdaBoost training with 500 iterations. FIG. 3(b) and FIG. 3(e) depict a map segmentation produced for the ? manual and the simplified segmentation, respectively, in the leave-one-out experiment. FIG. 3(c) and FIG. 3(f) depict a probability map produced for manual and the simplified segmentation, respectively.

Experiments

Data

The dataset used in this study is the canine leg muscle data from the SATA segmentation challenge (see paper to Asman et al. titled "MICCAI 2013 Segmentation Algorithms, Theory and Applications (SATA) Challenge Results Summary," MICCAI 2013 Challenge Workshop on Segmentation: Algorithms, Theory and Applications, Springer, 2013). So far, this dataset has been mostly applied for evaluating multi-atlas label fusion techniques. The dataset contains 45 canine leg MR scans (22 for training and 23 for testing). For each dog, images were acquired with two MR modalities: a T2-weighted image sequence was acquired using a variable-flip-angle turbo spin echo (TSE) sequence, and a T2-weighted fat-suppressed images (T2FS) sequence was then acquired using the same variable-flip-angle TSE sequence with the same scanning parameters except that a fat saturation preparation was applied. Seven proximal pelvic limb muscles were manually segmented: cranial sartorius(CS), rectus femoris(RF), semitendinosus(SE), biceps femoris(BF), gracilis(GR), vastus lateralis(VL) and adductor magnus(AD).

To make the comparison between different label fusion methods invariant to the performance of image registration, the challenge provides standard registration results produced by using the ANTs registration software (see the paper to Avants et al. titled "Symmetric Diffeomorphic Image Registration with Cross-Correlation: Evaluating Automated Labeling of Elderly and Neurodegenerative Brain," Medical Image Analysis, 12(1), 2008, pp. 26-41) between each training subject and each of the remaining (training and testing) subjects. Performance based on these standard registrations is reported.

Experimental Setup

For the canine leg muscle segmentation challenge using standard registration, so far the best published results were produced by using the joint label fusion (JLF) method (see the paper to Wang et al. titled "Multi-Atlas Segmentation with Joint Label Fusion," IEEE Trans. on PAMI, 35(3), 2013, pp. 611-623) combined with non-iterative corrective learning (see paper to Asman et al. titled "MICCAI 2013 Segmentation Algorithms, Theory and Applications (SATA) Challenge Results Summary," MICCAI 2013 Challenge Workshop on Segmentation: Algorithms, Theory and Applications, Springer, 2013). To facilitate a comparison with the current state of the art method, the joint label fusion method was used as the host method. Joint label fusion was applied with the parameters reported in the paper to Wang et al. titled "Multi-Atlas Segmentation with Joint Label Fusion," IEEE Trans. on PAMI, 35(3), 2013, pp. 611-623, i.e., patch radius $r_p=2$, searching radius $r_s=4$ and model parameter $\beta=0.5$, to produce the initial segmentation for each image. For each training image, its joint label fusion result was produced by using the remaining training images as the atlases. For the tested learning algorithms, a one-voxel dilation was applied to define working ROIs and a cubic neighborhood of size 5×5×5 was used to compute appearance and contextual features. For the present invention's method, AdaBoost was applied with 500 training iterations for deriving simplified segmentation problems at each iteration.

Next, a comparison was made with Auto-context learning. Auto-context is implemented through extending corrective learning as well. The only differences from the Path algorithm are that 1) no simplified segmentation problems are defined in each iteration; and 2) the Stacking technique is not applied. To evaluate the effectiveness of each component, a Stacked method was also tested, where the Auto-context algorithm is implemented with the Stacking technique, but still without defining simplified segmentation problems at each iteration.

Two experiments were conducted. The first experiment was a four-fold cross-validation on the 22 training subjects. In this test, the 22 training subjects were randomly divided into four non-overlapping groups. For cross-validation, each group was applied for testing once and the remaining groups were applied for training. In the second experiment, all training subjects were applied to train each method and the performance was evaluated on the 23 testing subjects. The evaluation results on the testing subjects were computed by the online evaluation system provided by the challenge organizer.

Figure 4:
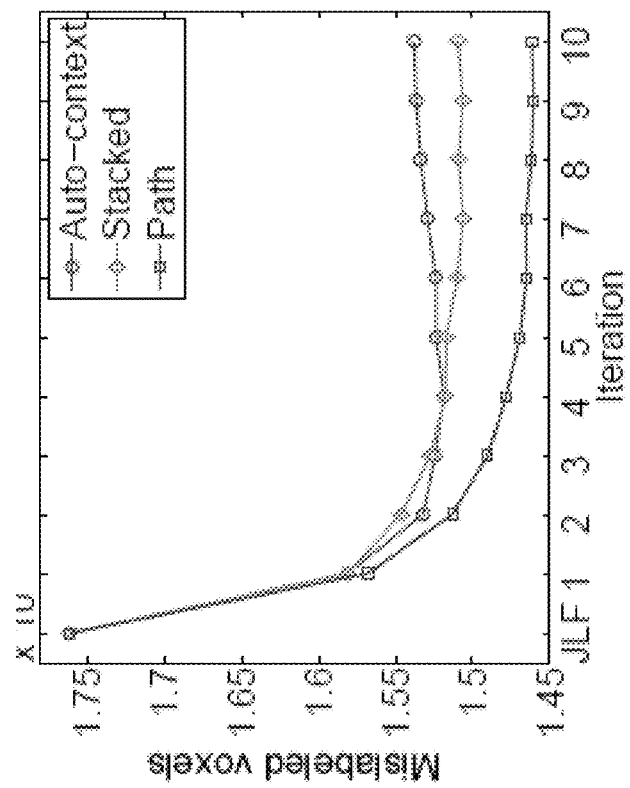
FIGS. 4(a)-(b) depict the performance of the joint label fusion and the performance of Auto-context, Stacked, Path at each iteration on the 4-fold cross-validation experiment.
Figure 4:
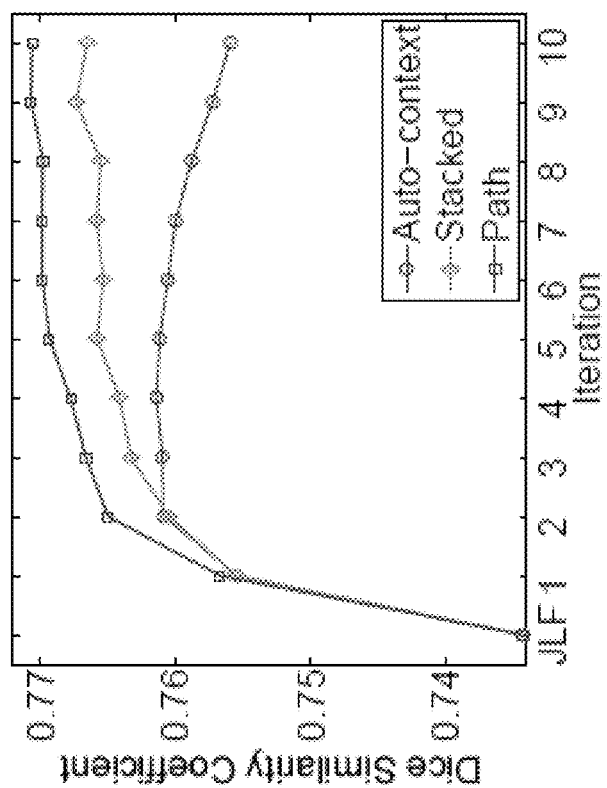

FIGS. 4(a)-(b) depict the performance of the joint label fusion and the performance of Auto-context, Stacked, Path at each iteration on the 4-fold cross-validation experiment. The performance is reported in Dice coefficient (see FIG. 4(a)) and average number of mislabeled voxels (FIG. 4(b)).

FIG. 5 depicts a table showing segmentation performance produced in the 4-fold cross-validation experiment for each anatomical region by joint label fusion, Auto-context, Stacked, and Path after 10 iterations, respectively. Results are measured using the Dice similarity coefficient.

Results

Figure 6:
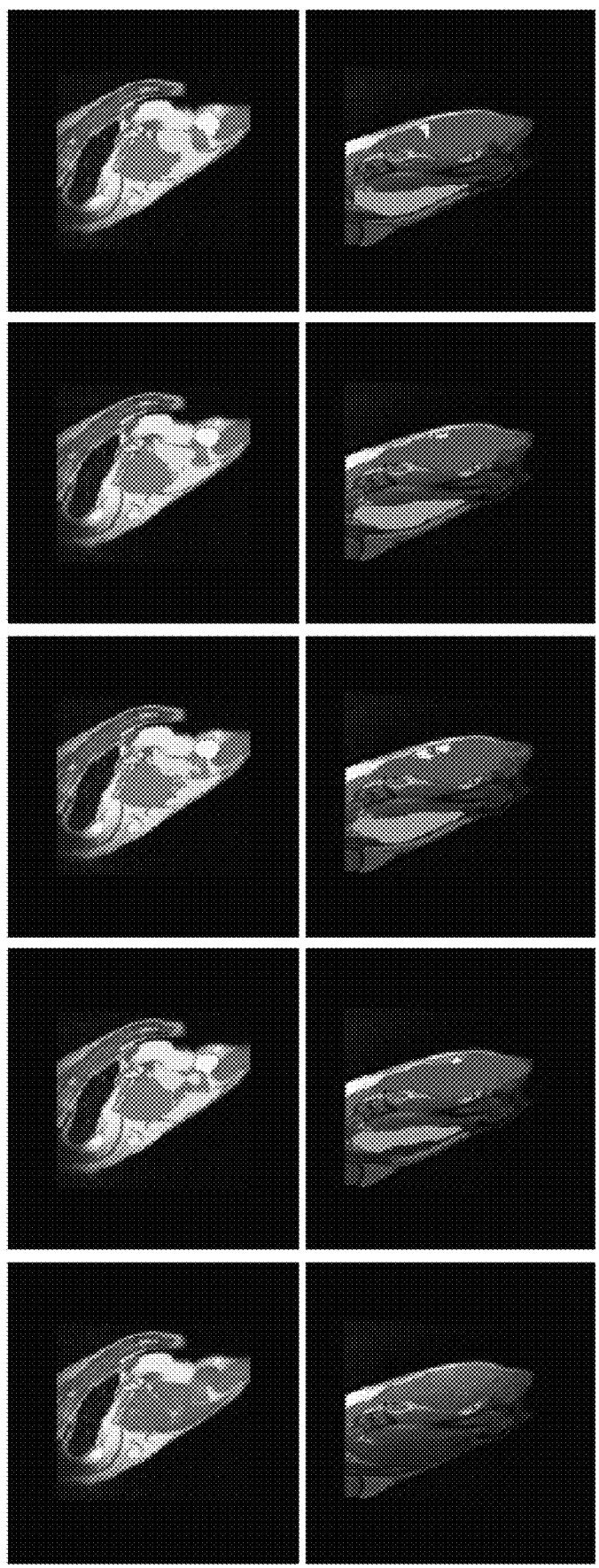
FIG. 6 depicts the segmentation produced by Auto-context, Stacked and Path after 10 iterations on the 4-fold cross-validation experiment.

FIGS. 4(a)-(b) show the overall segmentation performance produced in the four-fold cross-validation experiment by Auto-context, Stacked and Path, respectively. The performance of joint label fusion is given as a baseline. Note that the first iteration produced the most improvement for all three methods. The subsequent iterations produced further improvement but with diminishing improvement gains as the iteration increased. A performance drop was observed for Auto-context after 4 iterations, which indicates overfitting. In contrast, Stacked and Path showed more consistent improvement as iteration increases. One interesting finding is that the results produced by Auto-context and Stacked at the first iteration are slightly worse than those produced by Path. At the first iteration, each method has the same feature images and the only difference is that Path tries to predict a simplified segmentation problem, while Auto-context and Stacked try to predict the original manual segmentation. Hence, this result shows that employing a simplified segmentation problem actually improves the performance for predicting the original manual segmentation as well. A possible explanation is that the simplified segmentation problem may be less noisy than manual segmentation, which allows the learning algorithm to reach more optimal solution. FIG. 5 gives more details on the segmentation accuracy for each anatomical label produced by each method after 10 iterations. The improvement over Auto-context produced by Stacked and Path both are statistically significant, with $p<0.01$ and $p<0.0001$ on the paired Students t-test, respectively. The improvement over Stacked produced by Path is statistically significant with $p<0.02$ on the paired Students t-test. FIG. 6 depicts the segmentation produced by Auto-context, Stacked and Path after 10 iterations on the 4-fold cross-validation experiment.

The table shown in FIG. 7 outlines the segmentation performance produced for the 23 testing subjects by Auto-context, Stacked, and Path after 10 iterations on the 4-fold cross-validation experiment. This table shows the segmentation performance on the testing data produced by JLF, JLF+corrective learning, and Auto-context/Stacked/Path after 10 iterations, respectively. Results are reported in mean (median) Dice coefficient over all anatomical labels. The results produced by combining joint label fusion and corrective learning are so far the best published results on the canine leg muscle data using standard registration, which is provided as a baseline. Overall, Auto-context produced prominent improvement over the baseline, with 2% improvement in Dice coefficient. The proposed method produced 1.8% improvement over Auto-context.

It is shown that sequential learning based semantic segmentation methods can be interpreted as an approximation technique derived from a Bayesian formulation. To improve the effectiveness of applying this approximation technique, a Path algorithm is introduced that solves a segmentation problem by sequentially solving a series of simplified segmentation problems. To achieve this goal, a learning-based method is used to generate simplified segmentation problems by explicitly controlling the complexities of the modeling classifiers.

The complexity of the simplified segmentation problem at each iteration is a free parameter, which is controlled by AdaBoost training iteration in the present invention's method. Low complexity reduces the risk of inaccurate approximation caused by using the MAP solution to replace the Bayesian integration. However, it also makes the contextual features provided from solving the simplified problem less useful for solving the original problem. Hence, an optimal complexity is expected to balance the two considerations.

In yet another embodiment, the present invention provides an article of manufacture comprising non-transitory computer storage medium storing computer readable program code which, when executed by a computer, implements a computer-based medical image segmentation method for locating an anatomical structure in an image of interest to a user, using a training set of one or more annotated, anatomical images, the method comprising: (a) computer readable program code decomposing each annotated, anatomical image in the training set into a plurality of regions; (b) computer readable program code generating, for each annotated, anatomical image in the training set, a hierarchy that includes a plurality of levels, each level in the hierarchy corresponding to one of the plurality of regions; (c) computer readable program code obtaining, from storage, at least one previously derived annotation for each level in the hierarchy and training a plurality of first classifiers to approximate the previously derived annotations, wherein the first classifiers are trained in a particular sequence such that the output of one of the first classifiers becomes input to another one of the first classifiers; (d) computer readable program code storing the trained, first classifiers of (c); and (e) computer readable program code locating an anatomical structure in the image of interest to the user based on stored trained, first classifiers.

In yet another embodiment, the present invention provides an article of manufacture comprising a non-transitory computer storage medium storing computer readable program code which, when executed by a computer, implements a computer-based medical image segmentation method for locating an anatomical structure in an image of interest to a user, using a training set of one or more anatomical images, the method comprising: (a) computer readable program code decomposing each anatomical image in the training set into a plurality of regions; (b) computer readable program code generating, for each anatomical image in the training set, a hierarchy that includes a plurality of levels, each level in the hierarchy corresponding to one of the plurality of regions; (c) computer readable program code training, for each anatomical image in the training set, a plurality of first classifiers to approximate one or more annotations, and storing one or more such estimated annotations by the first classifiers as previously derived annotations; (d) computer readable program code training a plurality of second classifiers to approximate the previously derived annotations, where the second classifiers are trained in a particular sequence such that the output of one of the second classifiers becomes an input to another one of the second classifiers; (e) computer readable program code outputting trained, second classifiers in (d); and (f) computer readable program code locating an anatomical structure in the image of interest to the user based on stored trained, second classifiers.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

CONCLUSION

A system and method has been shown in the above embodiments for the effective implementation of a system, method and article of manufacture for finding a path for segmentation through sequential learning. While various preferred embodiments have been shown and described, it will be understood that there is no intent to limit the invention by such disclosure, but rather, it is intended to cover all modifications falling within the spirit and scope of the invention, as defined in the appended claims.

The invention claimed is:

1. A medical image segmentation method for locating an anatomical structure in an image of interest to a user, using a training set of one or more annotated, anatomical images, the method comprising:
  (a) decomposing each annotated, anatomical image in the training set into a plurality of regions;
  (b) generating, for each annotated, anatomical image in the training set, a hierarchy that includes a plurality of levels, each level in the hierarchy corresponding to one region of the plurality of regions;
  (c) obtaining, from storage, at least one previously derived annotation for each level in the hierarchy and training, via sequential training, a plurality of first classifiers to approximate the at least one previously derived annotation, wherein the first classifiers are trained in a particular sequence such that the output of one of the first classifiers becomes input to another one of the first classifiers, the at least one previously derived annotation estimated by a plurality of second classifiers, and wherein the sequential training of the first classifiers is based on an approximation technique derived from a Bayesian approximation of a probabilistic distribution of annotations;
  (d) storing the trained, first classifiers of (c); and
  (e) locating an anatomical structure in the image of interest to the user based on the stored trained, first classifiers.

2. The medical image segmentation method of claim 1, wherein the method comprises:
  training, for each anatomical image in the training set, the plurality of second classifiers to approximate one or more annotations; and
  storing the annotations approximated using the second classifiers as the at least one previously derived annotation.

3. The medical image segmentation method of claim 1, wherein a corrective learning technique is applied to the output of one of the first classifiers in order to correct annotation errors before becoming input to said another one of the first classifiers.

4. The medical image segmentation method of claim 1, wherein a leave-one-out cross-validation strategy is used to produce classification maps for each training image.

5. The medical image segmentation method of claim 1, wherein each anatomical image in the training set is decomposed into a plurality of regions based on a maximum a posteriori (MAP) segmentation procedure.

6. A medical image segmentation method for locating an anatomical structure in an image of interest to a user, using a training set of one or more anatomical images, the method comprising:
  (a) decomposing each anatomical image in the training set into a plurality of regions;
  (b) generating, for each anatomical image in the training set, a hierarchy that includes a plurality of levels, each level in the hierarchy corresponding to one of the plurality of regions;
  (c) training, for each anatomical image in the training set, a plurality of first classifiers to estimate one or more annotations, and storing the estimated one or more annotations by the first classifiers as previously derived annotations;
  (d) training, via sequential training, a plurality of second classifiers to approximate the previously derived annotations, where the second classifiers are trained in a particular sequence such that the output of one of the second classifiers becomes input to another one of the second classifiers, and wherein the sequential training of the second classifiers is based on an approximation technique derived from a Bayesian approximation of a probabilistic distribution of annotations;
  (e) storing the trained, second classifiers in (d); and
  (f) locating an anatomical structure in the image of interest to the user based on stored trained, second classifiers.

7. The medical image segmentation method of claim 6, wherein a corrective learning technique is applied to the output of one of the second classifiers in order to correct annotation errors before becoming input to said another one of the second classifiers.

8. The medical image segmentation method of claim 6, wherein a leave-one-out cross-validation strategy is used to produce classification maps for each training image.

9. The method of claim 6, wherein each anatomical image in the training set is decomposed into a plurality of regions based on a maximum a posteriori (MAP) segmentation procedure.

10. An article of manufacture comprising a non-transitory computer storage medium storing computer readable program code which, when executed by a computer, implements a computer-based medical image segmentation method for locating an anatomical structure in an image of interest to a user, using a training set of one or more annotated, anatomical images, the method comprising:
(a) computer readable program code decomposing each annotated, anatomical image in the training set into a plurality of regions;
(b) computer readable program code generating, for each annotated, anatomical image in the training set, a hierarchy that includes a plurality of levels, each level in the hierarchy corresponding to one region of the plurality of regions;
(c) computer readable program code obtaining, from storage, at least one previously derived annotation for each level in the hierarchy and training, via sequential training, a plurality of first classifiers to approximate the at least one previously derived annotation, wherein the first classifiers are trained in a particular sequence such that the output of one of the first classifiers becomes input to another one of the first classifiers, the at least one previously derived annotation estimated by a plurality of second classifiers, and wherein the sequential training of the first classifiers is based on an approximation technique derived from a Bayesian approximation of a probabilistic distribution of annotations;
(d) computer readable program code storing the trained, first classifiers of (c); and
(e) computer readable program code locating an anatomical structure in the image of interest to the user based on stored trained, first classifiers.

11. The article of manufacture of claim 10, wherein a corrective learning technique is applied to the output of one of the first classifiers in order to correct annotation errors before becoming input to said another one of the first classifiers.

12. The article of manufacture of claim 10, wherein the deriving step further comprises:
computer readable program code training the plurality of second classifiers to approximate one or more annotations for each anatomical image in the training set; and
computer readable program code storing the annotations approximated using the second classifiers as the at least one previously derived annotation.

13. The article of manufacture of claim 10, wherein a leave-one-out cross-validation strategy is used to produce classification maps for each training image.

14. The article of manufacture of claim 10, wherein each anatomical image in the training set is decomposed into a plurality of regions based on a maximum a posteriori (MAP) segmentation procedure.

15. An article of manufacture comprising non-transitory computer storage medium storing computer readable program code which, when executed by a computer, implements a computer-based medical image segmentation method for locating an anatomical structure in an image of interest to a user, using a training set of one or more anatomical images, the method comprising:
(a) computer readable program code decomposing each anatomical image in the training set into a plurality of regions;
(b) computer readable program code generating, for each anatomical image in the training set, a hierarchy that includes a plurality of levels, each level in the hierarchy corresponding to one of the plurality of regions;
(c) computer readable program code training, for each anatomical image in the training set, a plurality of first classifiers to estimate one or more annotations, and storing the estimated one or more annotations by the first classifiers as previously derived annotations;
(d) computer readable program code training, via sequential training, a plurality of second classifiers to approximate the previously derived annotations, where the second classifiers are trained in a particular sequence such that the output of one of the second classifiers becomes an input to another one of the second classifiers, and wherein the sequential training of the second classifiers is based on an approximation technique derived from a Bayesian approximation of a probabilistic distribution of annotations;
(e) computer readable program code outputting trained, second classifiers in (d); and
(f) computer readable program code locating an anatomical structure in the image of interest to the user based on stored trained, second classifiers.

16. The article of manufacture of claim 15, wherein a leave-one-out cross-validation strategy is used to produce classification maps for each training image.

* * * * *